United States Patent
Jameel et al.

(10) Patent No.: US 12,122,960 B1
(45) Date of Patent: Oct. 22, 2024

(54) PYROLYSIS OF LOW-DENSITY POLYETHYLENE USING A METAL-DOPED ZEOLITE

(71) Applicant: KING FAHD UNIVERSITY OF PETROLEUM AND MINERALS, Dhahran (SA)

(72) Inventors: Abdul Gani Abdul Jameel, Dhahran (SA); Nabeel Ahmad Javaid Ahmad, Dhahran (SA); Usama Ahmed Mehmood Ahmed, Dhahran (SA); Mohammad Nahid Siddiqui, Dhahran (SA); Aniz Chennampilly Ummer, Dhahran (SA); K. M. Oajedul Islam, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/753,666

(22) Filed: Jun. 25, 2024

(51) Int. Cl.
*C10G 1/10* (2006.01)
*B01J 29/40* (2006.01)
(Continued)

(52) U.S. Cl.
CPC .............. *C10G 1/10* (2013.01); *B01J 29/405* (2013.01); *B01J 29/46* (2013.01); *B01J 35/615* (2024.01); *B01J 35/633* (2024.01); *B01J 37/0201* (2013.01); *B01J 37/088* (2013.01); *B01J 37/30* (2013.01); *C07C 4/04* (2013.01);
(Continued)

(58) Field of Classification Search
CPC ........ C08J 11/10; C08J 2321/00; B01J 19/12; B01J 19/126; B01J 29/46; B01J 29/405; B01J 35/615; B01J 35/633; B01J 37/088; B01J 37/30; B01J 37/0201; C10G 1/00; C10G 1/10; C07C 4/22; C07C 4/04; C10B 57/06; C10B 53/07; C10B 19/00
See application file for complete search history.

(56) References Cited

U.S. PATENT DOCUMENTS

| | | |
|---|---|---|
| 9,200,207 B2 | 12/2015 | Huang et al. |
| 10,421,062 B2 | 9/2019 | Gaffney |

(Continued)

FOREIGN PATENT DOCUMENTS

| | | |
|---|---|---|
| CN | 117563661 A | 2/2024 |
| WO | 2024/015567 A2 | 1/2024 |

OTHER PUBLICATIONS

Zhang et al. (Production of monocyclic aromatics and light olefins through ex-situ catalytic pyrolysis of low-density polyethylene over Ga/P/ZSM-5 catalyst, 2023, Journal of the Energy Institute 108, 01235) (Year: 2023).*

(Continued)

*Primary Examiner* — Youngsul Jeong
(74) *Attorney, Agent, or Firm* — Oblon, McClelland, Maier & Neustadt, L.L.P.

(57) ABSTRACT

A method of converting a polymer including contacting a catalyst with a low-density polyethylene polymer to form a mixture and heating the mixture to a temperature of 200 degrees Celsius (° C.) to 600° C. in a microwave reactor to form a product. The catalyst includes an HZSM-5 zeolite, and 1 weight percent (wt. %) to 10 wt. % gallium and 0.1% to 5 wt. % copper, based on the total weight of the catalyst.

20 Claims, 21 Drawing Sheets

(51) Int. Cl.
    *B01J 29/46* (2006.01)
    *B01J 35/61* (2024.01)
    *B01J 35/63* (2024.01)
    *B01J 37/02* (2006.01)
    *B01J 37/08* (2006.01)
    *B01J 37/30* (2006.01)
    *C07C 4/04* (2006.01)
    *C07C 4/06* (2006.01)
    *C07C 4/22* (2006.01)
    *C10B 19/00* (2006.01)
    *C10B 53/07* (2006.01)
    *C10B 57/06* (2006.01)

(52) U.S. Cl.
    CPC .............. *C07C 4/22* (2013.01); *C10B 19/00* (2013.01); *C10B 53/07* (2013.01); *C10B 57/06* (2013.01); *C07C 2529/46* (2013.01); *C10G 2300/1003* (2013.01)

(56) References Cited

U.S. PATENT DOCUMENTS

2021/0347960 A1  11/2021  Hu et al.
2024/0131503 A1*  4/2024  Chareonpanich ........ B01J 23/08
2024/0182790 A1*  6/2024  Cheng ..................... B01J 29/46

OTHER PUBLICATIONS

Zhang et al. (Gasoline-range hydrocarbons produced from microwave-induced pyrolysis of low-density polyethylene over ZSM-5, 2015, Fuel, 144, 33-42) (Year: 2015).*

Hong et al. (Microwave heating performances of low density polyethylene (LDPE) plastic particles, 2021, Journal of Analytical and Applied Pyrolysis 160, 105356) (Year: 2021).*

Zhang et al. ; Production of monocyclic aromatics and light olefins through ex-situ catalytic pyrolysis of low-density polyethylene over Ga/P/ZSM-5 catalyst ; Journal of the Energy Institute, vol. 108 ; Jun. 2023 ; 6 Pages.

* cited by examiner

PYROLYSIS OF LOW-DENSITY POLYETHYLENE USING A METAL-DOPED ZEOLITE

STATEMENT OF PRIOR DISCLOSURE BY INVENTOR

Aspects of the present disclosure are described in K. M. O. Islam, "Microwave Catalytic Pyrolysis of Waste Plastic" Masters thesis, King Fahd University of Petroleum and Minerals; 2023, incorporated herein by reference in its entirety.

STATEMENT OF ACKNOWLEDGEMENT

Support provided by the Interdisciplinary Research Center for Refining and Advanced Chemicals at King Fahd University of Petroleum and Minerals (KFUPM) under funded project INRC2203 is gratefully acknowledged.

BACKGROUND

Technical Field

The present disclosure is directed towards catalytic pyrolysis of polymers, and particularly, to a catalytic pyrolysis of a low-density polyethylene polymer using a metal-doped zeolite.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Plastic materials, which are highly versatile, durable, and cost-effective synthetic organic polymers, play a role in daily life. Among them, polyethylene (PE) is commonly used and accounts for 29% of the total plastic demand. PE is used in a plurality of sectors, such as health, food, and agriculture, with high demand. Recently, consumption of plastics has significantly risen, and the majority of these plastics may end up in landfills or the natural environment, resulting in the wastage of resources and causing environmental damage. Plastic waste contains high-quality energy due to its high carbon content, and improper disposal can lead to the wastage of resources. Chemical conversion of plastic waste into high-quality fuels or value-added chemicals is a viable option to meet the growing energy demand.

Pyrolysis is a chemical conversion technique used to treat plastic waste and produce valuable fuels without the presence of oxygen. Pyrolysis is environmentally friendly and follows the closed-loop approach. In particular, microwave pyrolysis is a promising technology for solid waste treatment due to its advantages over conventional pyrolysis. Pyrolysis may directly heat a material by exciting the molecules, resulting in rapid and efficient heating. Unlike conventional heating methods that rely on conduction or convection, microwave heating is volumetric, meaning it heats the material throughout its entire volume simultaneously. This leads to faster heat transfer and reduced processing times. Moreover, under microwave irradiation, heavy hydrocarbons are more easily broken down into lighter fractions due to the reduced processing time and localized heating.

Linear density polyethylene (LDPE), a type of PE, is a major contributor to plastic waste, and converting PE into useful fuels and chemicals may be preferable due to weak intermolecular forces present in LDPE. The resulting pyrolysis oil from LDPE is of high quality as it is free of oxygen, acids, and water and has a high carbon and hydrogen content. However, the chemical profile of LDPE pyrolysis oil is complex and varied. To produce refined chemical fuels, the crude pyrolysis oil must undergo further processing using adaptable catalysts that may narrow down the spectrum of product distribution and increase selectivity for valuable chemical products. When catalysts are introduced into the process of thermal breakdown of polymers, it can enhance the reaction rate in comparison to the polymer's pyrolysis without catalysts. Additionally, the incorporation of catalysts in pyrolysis can improve the characteristics of the resulting liquid products. Solid acid catalysts like zeolites are commonly used in catalytic pyrolysis or upgrading processes because they are widely used in the petroleum industry. These have been examined for their exceptional efficiency and endurance in breaking down plastic waste into fuel oil/chemicals. One such catalyst, ZSM-5 zeolite, is highly effective in polyethylene degradation due to its strong acidity, primarily exhibiting high efficiency in aromatization. Other catalysts like natural zeolite, Y-zeolite, HZSM-5, Al-MCM-41, a mixture of HZSM-5 & MCM-41, MgO, and metal-doped natural zeolite have been the subject of research for the pyrolysis, of waste plastics.

Various studies make use of different types of zeolite-based catalysts to improve the pyrolysis oil quality yield, however, the studies do not incorporate the use of metal-doped zeolites for the pyrolysis of plastic materials under microwave irradiance. Zeolites in the H-form display limited energy absorption, whereas certain zeolites containing Na and K may absorb enough energy to reach a melting point within a few minutes. Consequently, zeolite samples containing metals have a propensity to absorb microwave energy and undergo self-heating. Metal-impregnated zeolite possesses both acid sites and metal sites where aluminasilicate supports provide acid sites and supported metals like Ni, Cu, Co, or their mixtures provide metal sites. Moreover, the addition of a second metal brings variations on the basic properties of a zeolite-based catalyst.

There remains a need for a catalyst with improved efficiency and product selectivity. Hence, it is one object of the present disclosure to provide a method for reducing polymers with a metal-doped zeolite.

SUMMARY

In an exemplary embodiment, a method of converting a polymer is described. The method includes contacting a catalyst with a low-density polyethylene polymer to form a mixture and heating the mixture to a temperature of 200 degrees Celsius (° C.) to 600° C. in a microwave reactor to form a product. The yield of the product is 20 weight % to 99 weight % gas and 1 weight % to 30 weight % liquid based on a total weight of the gas, the liquid and coke in the product. The catalyst includes an HZSM-5 zeolite, and 1 weight percent (wt. %) to 10 wt. % gallium and 0.1% to 5 wt. % copper, based on a total weight of the catalyst.

In some embodiments, the catalyst has a Brunauer-Emmett-Teller (BET) surface area of 250 square meter per gram ($m^2/g$) to 350 $m^2/g$.

In some embodiments, the catalyst has a pore volume of 0.01 cubic centimeter per gram (cm³/g) to 0.1 cm³/g.

In some embodiments, the catalyst is crystalline.

In some embodiments, the gallium and the copper are present in pores of the HZSM-5 zeolite.

In some embodiments, the catalyst includes 50-60 wt. % 0, 30-40 wt. % Si, 1-5 wt. % Al, 1-10 wt. % Ga and 0.1-5 wt. % Cu, based on a total weight of the catalyst.

In some embodiments, particles of the catalyst have an average size of 1 micrometers (μm) to 100 μm.

In some embodiments, the particles of the catalyst are aggregated.

In some embodiments, the mixture includes a weight ratio of the catalyst to the low-density polyethylene polymer of 1-15 to 1-15.

In some embodiments, the method includes heating the mixture in an absence of oxygen.

In some embodiments, the method of heating the mixture is for 1-60 minutes.

In some embodiments, the mixture further includes at least one selected from the group consisting of silicon carbide, activated carbon, graphite, and alumina.

In some embodiments, the yield of the product is less than 1 weight % coke.

In some embodiments, the gas is at least one selected from the group consisting of hydrogen, an alkane having 1-5 carbons, and an olefin having 2-4 carbons.

In some embodiments, the liquid is at least one selected from the group consisting of aromatic compounds having 9-12 carbons, aromatic compounds having 13-17 carbons, olefins having greater than 9 carbons, paraffins having greater than 9 carbons, and other aliphatics.

In some embodiments, the liquid is about 90% aromatic compounds having 9-12 carbons. In some embodiments, the gas is 15 volume percent (vol. %) to 20 vol. % hydrogen, based on a total volume of the gas.

In some embodiments, the hydrogen is collected and used to power the microwave reactor.

In some embodiments, the low-density polyethylene polymer is a waste product.

In some embodiments, the low-density polyethylene polymer has a density of from 0.91-0.93 g/cm³, and during the heating, the microwave reactor contains only the catalyst, a silicon carbide microwave adsorbent, the low-density polyethylene polymer and the product.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
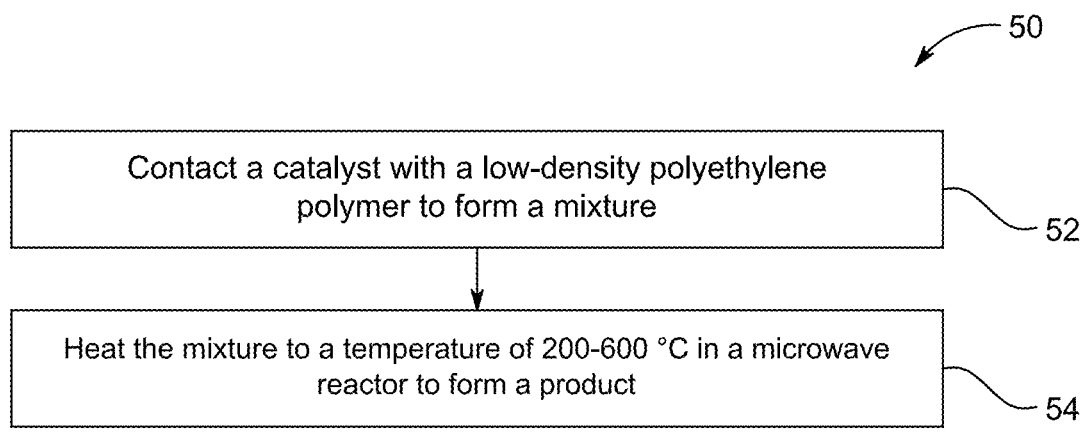
FIG. 1A is a flowchart illustrating a method of converting a polymer, according to certain embodiments.

In the drawings, reference numerals designate identical or corresponding parts throughout the several views. Further, as used herein, the words "a," "an," and the like generally carry a meaning of "one or more," unless stated otherwise.

Where a numerical limit or range is stated herein, the endpoints are included. Also, all values and subranges within a numerical limit or range are specifically included as if explicitly written out.

Furthermore, the terms "approximately," "approximate," "about," and similar terms generally refer to ranges that include the identified value within a margin of 20%, 10%, or preferably 5%, and any values therebetween.

As used herein, the term "aromatic compounds" refer to organic compounds characterized by the presence of one or more benzene rings in their structure. Some common aromatic compounds include benzene ($C_6H_6$), toluene (methylbenzene), xylene (dimethylbenzene), phenol, aniline, and nitrobenzene.

Aspects of the present disclosure are directed to microwave-assisted catalytic pyrolysis of low-density polyethylene (LDPE) to yield pyrolysis-derived oil. The catalytic pyrolysis was carried out using a catalyst including a gallium-doped zeolite, which is further doped with nickel, cobalt, or copper. The examples disclosed herein show that copper-impregnated gallium-doped zeolite (GCuZ3) catalyst provides superior catalytic activity compared to gallium-doped zeolite impregnated with nickel and cobalt.

FIG. 1A illustrates a schematic flow chart of a method of converting a polymer. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes contacting a catalyst with a polymer to form a mixture. The catalyst includes a zeolitic material. As used herein, the term "zeolitic material" or "zeolitic framework" refers to a material having the crystalline structure or three-dimensional framework of, but not necessarily the elemental composition of, a zeolite. Zeolites are porous silicate or aluminosilicate minerals that occur in nature. Elementary building units of zeolites are $SiO_4$ (and if appropriate, $AlO_4$) tetrahedra. Adjacent tetrahedra are linked at their corners via a common oxygen atom, which results in an inorganic macromolecule with a three-dimensional framework (frequently referred to as the zeolite framework). The three-dimensional framework of a zeolite also includes channels, channel intersections, and/or cages having dimensions in the range of 0.1-nanometers (nm), preferably 0.2-5 nm, more preferably 0.2-2 nm. Water molecules may be present inside these channels, channel intersections, and/or cages. Zeolites that are devoid of aluminum may be referred to as "all-silica zeolites" or "aluminum-free zeolites." Some zeolites which are substantially free of, but not devoid of, aluminum is referred to as "high-silica zeolites". Sometimes, the term "zeolite" is used to refer exclusively to aluminosilicate materials, excluding aluminum-free zeolites or all-silica zeolites.

In some embodiments, the zeolitic material has a three-dimensional framework that is at least one zeolite framework selected from the group consisting of a 4-membered ring zeolite framework, a 5-membered ring zeolite framework, a 6-membered ring zeolite framework, a 10-membered ring zeolite framework, and a 12-membered ring zeolite framework. The zeolite may have a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g., analcime, leucite, pollucite, and wairakite), phillipsite framework (e.g., harmotome), gismondine framework (e.g., amicite, gismondine, garronite, and gobbinsite), chabazite framework (e.g., chabazite-series, herschelite, willhendersonite, and SSZ-13), faujasite framework (e.g., faujasite-series, Linde type X, and Linde type Y), mordenite framework (e.g., maricopaite and mordenite), heulandite framework (e.g., clinoptilolite and heulandite-series), stilbite framework (e.g., barrerite, stellerite, and stilbite-series), brewsterite framework, or cowlesite framework.

In some embodiments, the zeolitic material having a zeolite framework is selected from the group consisting of ZSM-5, ZSM-8, ZSM-11, ZSM-12, ZSM-18, ZSM-23, ZSM-35 and ZSM-39. In a preferred embodiment, the zeolitic material is ZSM-5. In some embodiments, the ZSM-5 has a formula of $Na_nAl_nSi_{96-n}O_{192}\cdot 16H_2O$, where n is an integer from 0 to 27, preferably 1, 2, 3, 4, 5, 6, 7, 8, 9, 10, 11, 12, 13, 14, 15, 16, 17, 18, 19, 20, 21, 22, 23, 24, 25, or 26. ZSM-5 is composed of several pentasil units linked together by oxygen bridges to form pentasil chains. A pentasil unit consists of eight five-membered rings. In these rings, the vertices are Al or Si and an O is assumed to be bonded between the vertices. The pentasil chains are interconnected by oxygen bridges to form corrugated sheets with 10-ring holes. Like the pentasil units, each 10-ring hole has Al or Si as vertices with an O assumed to be bonded between each vertex. Each corrugated sheet is connected by oxygen bridges to form a structure with straight 10-ring channels running parallel to the corrugations and sinusoidal 10-ring channels perpendicular to the sheets. Adjacent layers of the sheets are related by an inversion point.

In some embodiments, pore channels of the ZSM-5 contain a cationic ion exchange group. In a preferred embodiment, in ZSM-5 the cationic ion exchange group is ammonium ($NH_4^+$). In some embodiments, the ammonium cationic ion exchange group is transitioned to $H^+$ to form (HZSM-5). In a preferred embodiment, HZSM-5 is prepared by calcining ZSM-5 powder at a temperature range of 500-600° C., preferably 550° C., to obtain HZSM-5. In some embodiments, HZSM-5 has an MFI framework structure.

In some embodiments, HZSM-5 has numerous acidic sites on zeolite surfaces. These $H^+$ ions readily exchange with metal ions. As metal concentrations rise, they replace $H^+$ ions and occupy zeolite structure channels. In some embodiments, the metal ions are selected from the group consisting of Gallium (Ga), Indium (In), Scandium (Sc), Titanium (Ti), Vanadium (V), Chromium (Cr), Manganese (Mn), Iron (Fe), Cobalt (Co), Nickel (Ni), Copper (Cu), and Zinc (Zn). In other words, the exchange of the $H^+$ in HZSM-5 with a metal ion results in doping of the metals in the zeolite pores. In a preferred embodiment, the HZSM-5 is doped with at least two metals. In a preferred embodiment, the HZSM-5 is doped with Ga and at least one selected from the group consisting of Cu, Co, and Ni. In a preferred embodiment, the HZSM-5 is doped with gallium and copper. In some embodiments, the gallium and the copper are present in pores of the HZSM-5 zeolite.

In an embodiment, the catalyst includes 1-10 wt. % of gallium, preferably including 1, 2, 3, 4, 5, 6, 7, 8, 9, 10 wt. % of gallium, and most preferably of about 5 wt. % gallium; and 0.1-5 wt. % of a second metal, preferably including 0.1, 0.2, 0.3. 0.4. 0.5, 0.6. 0.7, 0.8, 0.9, 1, 2, 3, 4, 5 wt. % of the second metal, more preferably including 1.5-3.5 wt. % of the second metal, and yet more preferably of about 2 wt. % the second metal, based on the total weight of the catalyst. In an embodiment, the catalyst includes 1-10 wt. % of gallium, preferably including 1, 2, 3, 4, 5, 6, 7, 8, 9, 10 wt. % of gallium, and most preferably of about 5 wt. % gallium; and 0.1-5 wt. % of copper, preferably including 0.1, 0.2, 0.3. 0.4. 0.5, 0.6. 0.7, 0.8, 0.9, 1, 2, 3, 4, 5 wt. % of copper, more preferably including 1.5-3.5 wt. % of copper, and yet more preferably of about 2 wt. % copper, based on the total weight of the catalyst.

In some embodiments, the catalyst includes 50-60 wt. %, more preferably 53 to 56 wt. %, and yet more preferably 54.58 wt. % O; 30-40 wt. %, more preferably 33 to 35 wt. %, and yet more preferably 34.62 wt. % Si; 1-5 wt. %, more preferably 2 to 4 wt. %, and yet more preferably 2.14 Al wt. %; 1-10 wt. %, more preferably 2 to 4 wt. %, and yet more preferably 3.36 wt. % Ga; and 0.1-5 wt. %, more preferably 2 to 4 wt. %, and yet more preferably 2.45 wt. % Cu, based on the total weight of the catalyst.

In some embodiments, the catalyst has a Brunauer-Emmett-Teller (BET) surface area of 250-350 meter square per gram (m$^2$/g), more preferably 290 to 320 m$^2$/g, and yet more preferably 300.5 m$^2$/g. The catalyst has a pore volume of 0.01-0.1 cubic centimeters per gram (cm$^3$/g), more preferably 0.105 cm$^3$/g. In some embodiments, the catalyst has both mesopores (2-50 nm) and micropores (less than 2 nm). In some embodiments, the catalyst is crystalline. In some embodiments, the particles of the catalyst have an average size of 1-100 micrometers (μm), preferably 10-90 μm, 20-80 μm, 30-70 μm, or 40-60 μm. In some embodiments, the particles of the catalyst are aggregated.

The catalyst is contacted with a polymer to obtain a mixture. In some embodiments, the polymer is selected from the group consisting of polyethylene (PE), polypropylene (PP), polyvinyl chloride (PVC), polystyrene (PS), nylon, teflon (polytetrafluoroethylene), and thermoplastic polyurethane (TPU). In some embodiments, the PE is low-density polyethylene (LDPE) or high-density polyethylene (HDPE). LDPE has more branching than HDPE, thus resulting in a structure having a lower density of 0.90-0.94 g/cm$^3$, preferably 0.91-0.93 g/cm$^3$, a lower crystallinity and a lower melting point of about 115° C. In some embodiments, the LDPE has a melt index of 1.5-2.7, 1.6-2.6, 1.7-2.5, and 1.8-2.4 and an average MW of 70,000 to 100,000, 75,000 to 95,000, or 80,000 to 90,000. In a preferred embodiment, the LDPE is a waste LDPE from for example, plastic bags, light packaging materials, wash bottles, corrosion protection layer for work surfaces, or computer hardware covers and packaging.

In the mixture, a weight ratio of the catalyst to the polymer is in the range of 1:20 to 20:1, preferably 1:18 to 18:1, preferably 1:15 to 15:1, preferably 1:12 to 12:1, preferably 1:10 to 10:1. In a most preferred embodiment, the weight ratio of the catalyst to the polymer is about 1:15.

At step 54, method 50 includes heating the mixture to 200-600° C., more preferably 250 to 550° C., and yet more preferably 500° C., in a reactor to form a product. In some embodiments, the reactor is selected from the group consisting of a fluidized bed reactor, a batch reactor, or a microwave reactor. In a preferred embodiment, the reactor is a microwave reactor. To prevent any unwanted side reactions, it is preferred to carry out the heating process in an inert atmosphere without oxygen, preferably under nitrogen or argon. Further, the process does not include any acids or water.

The heating is for 1-60 minutes, preferably 18 to 25 minutes, and yet more preferably 20 minutes. In some embodiments, the microwave reactor is run at a maximum power output of about 800-1000 watts (W) for about 1-5 minutes. In some embodiments, an adsorbent selected from silicon carbide, activated carbon, graphite, and alumina is placed inside the microwave reactor. In a preferred embodiment, the adsorbent is silicon carbide. During the heating process, the microwave reactor contains only the catalyst, the adsorbent, the polymer, and some amount of product, the yield of which is dependent on the heating time.

The heating process results in the formation of a product. The yield of the product is about 20-99% gas, preferably 25-95%, 30-90%, 35-85%, 40-80%, 45-75%, 50-70%, 55-65% gas and 1-30% liquid, preferably 5-25%, or 10-20% liquid. In some embodiments, the gas may include but are not limited to, carbon monoxide, carbon dioxide, methane, and various hydrocarbons. In some embodiments, the gas may be hydrogen, an alkane having 1-5 carbons, such as methane, ethane, propane, and butane, and an olefin having 2-4 carbons, such as propane, ethene, butene, and pentene. In a preferred embodiment, the gas product has a volume percentage of hydrogen in the total volume of the gas of about 15-20 vol. %, preferably 16-19 vol. %, or 17-18 vol. %.

The liquid product may include aromatic compounds having 9-12 carbons, such as naphthalene; aromatic compounds having 13-17 carbons; olefins having greater than 9 carbons, such as 1-decene, 1-dodecane, 1-tetradecane; paraffin having greater than 9 carbons, and other aliphatics such as hexane, heptane, octane, nonane. In a preferred embodiment, the liquid includes about 90% aromatic compounds having 9-12 carbons. In a preferred embodiment, the yield of the product is less than 1% coke.

In some embodiments, the microwave reactor is powered by a green energy source such as solar, wind, or hydrogen gas. In some embodiments, the hydrogen gas product is collected and used to power the microwave reactor.

While not wishing to be bound to a single theory, it is though that the Ga and Cu doped HZSM-5 produces the most C9-12 aromatics due to the catalytic activity of Cu, which promotes the formation of aromatic compounds through various reactions, including cyclization and aromatization. The combination of Ga and Cu also leads to synergistic effects that enhance the aromatization of hydrocarbons, resulting in a higher yield of C9-12 aromatics.

EXAMPLES

The following examples demonstrate a method of converting a polymer. The examples are provided solely for illustration and are not to be construed as limitations of the present disclosure, as many variations thereof are possible without departing from the spirit and scope of the present disclosure.

Example 1: Materials

A low-density polyethylene (LDPE) grade, 5SABIC® LDPE HP0823NN by SABIC, was used as feedstock. High-performance silicon carbide balls with 4 millimeters (mm) diameter were used as microwave absorbents supplied by Xinzhou Bearing Industrial, China. Zeolite catalyst (CBV 3024 E), with a SiO$_2$/Al$_2$O$_3$ molar ratio of 30 supplied by Zeolyst International, USA, was used as parent zeolite for metal doping. Gallium nitrate hydrate, nickel nitrate hexahydrate, Co hydrate hexahydrate, and copper nitrate trihydrate from Sigma Aldrich were metal precursors for modifying the zeolites.

Example 2: Catalyst Preparation

All catalytic preparations began with the NH$_4$-form of the ZSM-5 powder. ZSM-5 powder was calcined at 550 degrees Celsius (° C.) for 5 hours to transform it into the HZSM-5 powder, denoted as Z3. Transitioning from NH$_4^+$ to H$^+$ generates numerous acidic sites on zeolite surfaces. These H$^+$ ions readily exchange with metal ions. As metal concentrations rise, they replace H$^+$ ions and occupy zeolite structure channels. Gallium nitrate hydrate in an aqueous medium was used to incorporate 5% weight by weight (w/w) gallium (Ga) onto Z3 support material employing a wet impregnation step followed by evaporation to dryness. In particular, to prepare GZ3, 3 grams (g) of Z3 was added to a required volume of 0.5 molar (M) aqueous solution of gallium nitrate hydrate, then made up to a 100 milliliters (ml) volume and stirred for 4 hours at room temperature. Further, the suspension was gently heated at 60° C. overnight while being stirred to gradually evaporate water completely. The powder was collected, dried at 100° C. for 8 hours, then calcined at 550° C. for 5 hours and heated at 5 degrees Celsius per minute (° C./min). This sample is referred to as GZ3.

Bimetallic catalysts containing 5% w/w Ga and 2% w/w of either nickel (Ni), cobalt (Co), or copper (Cu) using the same support, Z3, were prepared. For their synthesis, a wet co-impregnation evaporation method was followed, which involves mixing both the metal precursor solutions together, and the same steps as that of GZ3 were completed. The bimetallic samples are referred to as GNiZ3, GCoZ3, and GCuZ3, containing Ni, Co, and Cu, respectively. The calcined samples were directly used as catalyst material.

Example 3: Microwave Pyrolysis Reactor Setup and Procedure

Figure 1B:
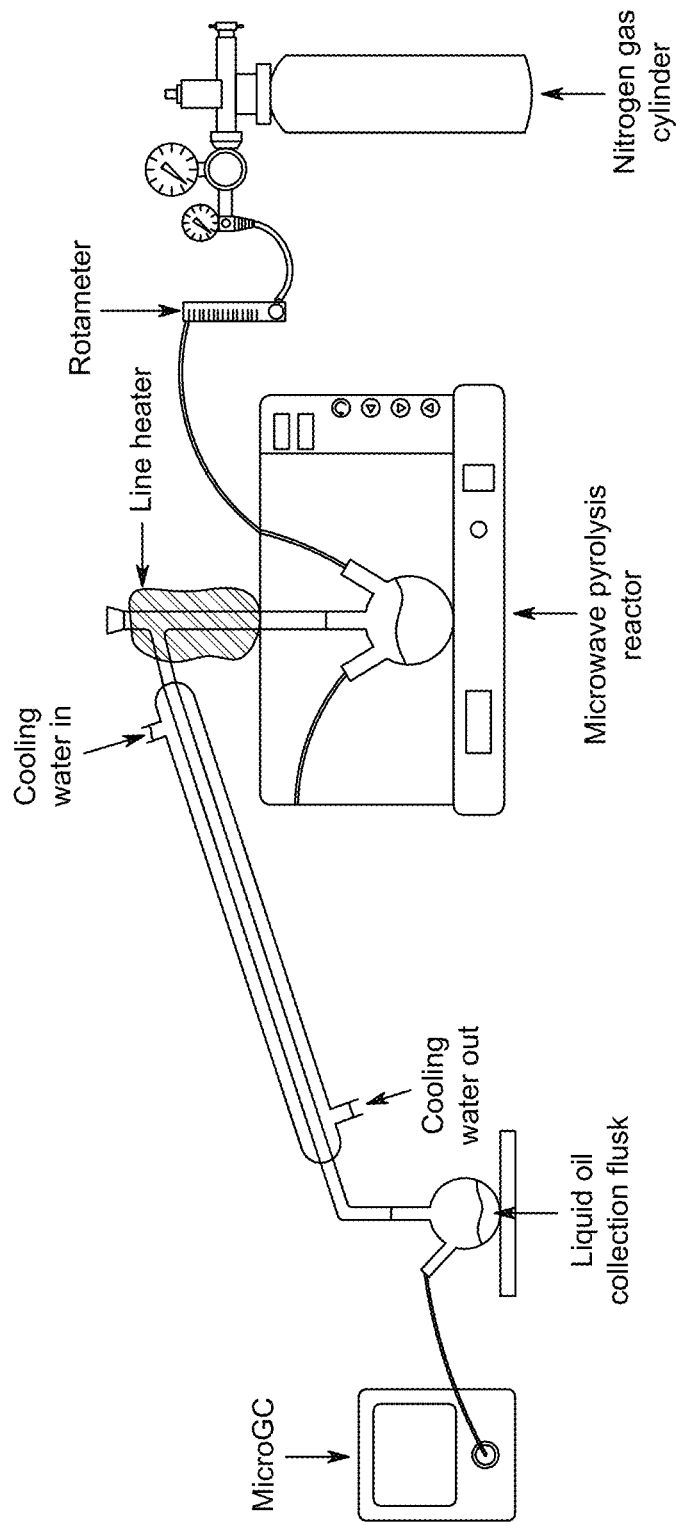
FIG. 1B is a schematic illustration of an experimental setup of a microwave pyrolysis reactor, according to certain embodiments.

The pyrolysis was conducted in an MCR-3SX type microwave chemical reactor with an output power of about 900 W (automatic frequency adjustable) and about 2450 megahertz (MHz) frequency, including a continuous output mode feature. A schematic of the experimental setup is illustrated in FIG. 1B. The whole microwave pyrolysis system was developed, including four main components for analyzing the sample. The aforementioned microwave pyrolysis system includes a quartz pyrolysis reactor, a set of temperature controllers (type K thermocouple & IR based) to measure the temperature at different points, and a condensation apparatus to collect the oil product and the microwave reactor.

The selected LDPE feedstock was pulverized using Pulverisette 19. A high-performance ball-type silicon carbide (SiC) absorbent was mixed with LDPE and catalyst and placed inside the 500 ml quartz flask. The amount of silicon carbide was fixed at 400 g to absorb the microwave radiation. The high SiC content demonstrated favorable properties for proper microwave absorption. For every run, 15 g of LDPE was weighed and mixed with 1 g of selected catalyst. For all the run, the catalyst and feedstock ratio were maintained at 1:15. The initial run was conducted as a blank run without a catalyst. The condensable gases were converted into wax inside the condensing line during this process. Almost no liquid oil was achieved in this case. Consequently, the run conducted without a catalyst was disregarded for subsequent characterization. The quartz flask was wrapped with glass wool and Teflon tape to avoid heat loss during the microwave radiation. Borosilicate glass connectors were used to connect the reactor outlet and the condenser. The connecting line was wrapped with a heating element and a temperature controller system to avoid condensation of the pyrolysis vapor. A temperature controller was developed to regulate the heating line temperature up to 500° C.; as such, the temperature was maintained at 250° C. This connecting line was connected to the condensing line. The cooling operation was accomplished by LAUDA MGW RC-20, which offers a reliable, compact, and energy-saving circulation chilling operation. The cooling water temperature was maintained at 5° C. An exit of the condensing line was linked to a collection flask with a round bottom, which was immersed in an ice bath to condense the condensable gases. All connections and joints were wrapped with Teflon tape, and leak tests were carried out to verify that there were no leaks.

A vacuum pump was used to evacuate the system, and nitrogen gas was supplied into the system at a rate of 200 milliliters per minute (ml/min) for 15 minutes before the pyrolysis reaction to maintain an oxygen-free environment. Before the operation, the nitrogen gas flow rate was reduced to 80 ml/min and kept constant. The final exit tube from the oil collection flask was placed in a water beaker to check for the presence of nitrogen gas, which was confirmed by the formation of bubbles.

Figure 2:
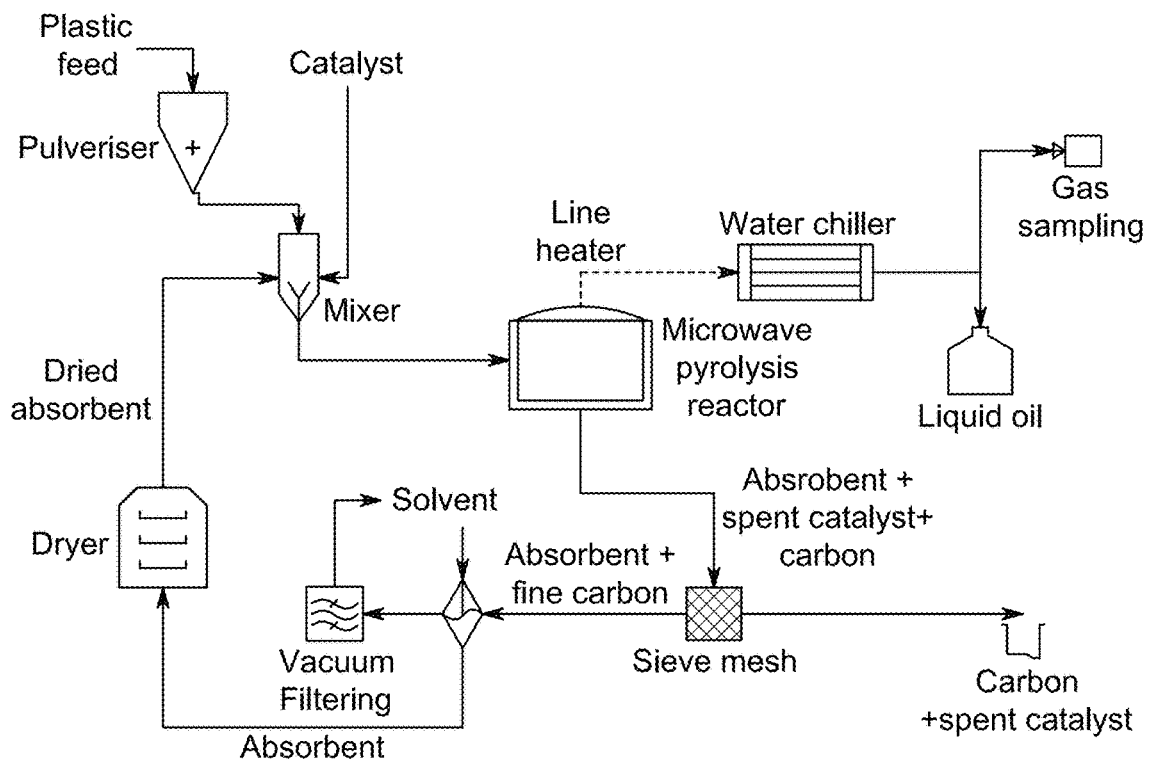
FIG. 2 is a process flow diagram of microwave-assisted pyrolysis of linear density polyethylene (LDPE), according to certain embodiments.

The reactor was started after ensuring all conditions for the nitrogen gas, heating, and condensing lines were met. To reach the pyrolysis temperature of 500° C. The microwave reactor was run at a maximum power output of about 900 watts (W) for the first five minutes. Ball-type high-performance silicon carbide is an excellent microwave radiation absorbent at 100° C./min, and the heating rate was achieved at maximum microwave power. Once it reached the desired pyrolysis temperature, the reactor was set to low microwave power of about 100 W. At low microwave power, the reaction run time was set to 20 minutes to confirm all the volatile parts of the plastic sample vaporized. The condensable liquid was collected as pyrolysis oil from the collection flask. The non-condensable vapors escaped as gas at the end of the condensers and were collected in gas bags for analysis. The spent catalyst and coke were separated from the absorbent by mesh sieving. Furthermore, fine carbon from the absorbent was separated using an addition of n-hexane solvent. Then, the wet absorbent was dried at 120° C. in a forced convection oven (JSOF-100, Korea) with a capacity of about 100 liters, JSOF-100. Absorbent was recovered in this way and used for the next cycle. The solvent was also recovered by vacuum filtering. Each experiment was repeated to confirm the accuracy and reproducibility of the initial findings. Details of this process flow are illustrated in FIG. 2.

The weight of the gas was calculated using the following equation:

Weight of gas=weight of plastic−weight of liquid−weight of coke

Example 4: Feedstock Characterization

The thermal degradation behavior of LDPE was characterized by simultaneous thermogravimetric analysis with a differential scanning calorimetry (TGA-DSC) analyzer (Model No. SDT Q600, V20.9, Build 20). Further, 8.9 mg of LDPE sample was taken to execute the experiment. The nitrogen flow rate was maintained at 50 ml/min throughout the operation. The temperature ramp was maintained at 10° C./min to reach 700° C. starting from room temperature.

Example 5: Pyrolysis Oil Characterization

A gas chromatography (GC) (Shimadzu GC Model 2020) equipped with a flame ionization detector (FID) was used to execute the simulated distillation (SimDist) of the pyrolysis oil samples. SimDist is a chromatographic procedure that translates retention times into boiling points. The detector temperature was maintained at 400° C. High-purity nitrogen gas was used as a carrier gas with a flow rate of 10 ml/min, and 1 microliter (µL) of diluted sample was infused into the injector at about 350° C. Furthermore, to identify and quantify the chemical compounds present in the oil, a gas chromatography-mass spectrometry (GC-MS) (GC-6890N/ 5975B and MSD) analysis was performed using an instrument from Agilent technologies. The oil sample was first diluted with chloroform, and 1 μL of the diluted sample was injected into the GC-MS instrument. The injector was set to a temperature of 280° C., pressure of 1.06 pascals per square inch (psi), and total flow rate of 10.4 ml/min. Helium gas was continuously supplied throughout the analysis, and the split ratio was maintained at 5:1.

Proton nuclear magnetic resonance ($^1$H NMR) analysis of the oil sample was conducted using a JEOL 600 MHz NMR spectrometer (JEOL USA). Chloroform (CDCl$_3$) was used as a deuterated solvent for the $^1$H NMR. The oil sample was dissolved in CDCl$_3$, and the resulting mixture was placed into a standard 5 mm NMR tube. Functional groups in the pyrolysis oil were identified using the Fourier transform infrared (FTIR) technique, conducted with a Nicolet 6700 model instrument. A KBr pellet was used to mount a drop of the oil, and the FTIR spectra were recorded in the range of wave numbers from 4000 cm$^{-1}$ to 400 cm$^{-1}$.

Example 6: Catalyst characterization

TGA-DSC was used to determine the coke content of the spent catalyst; around 5 mg of the spent catalyst sample was taken on an alumina pan, and pure air was purged with a flow rate of 200 ml/min to accomplish the operation for each sample. The temperature ramp was maintained at 20° C./min to reach 800° C., starting from room temperature. Further, morphological analysis of spent catalyst was done by scanning electron microscopy (SEM), IEM 11+ Desktop SEM, combining 3 different micro-analytical detectors, SE, BSE and EDS (Supplier: Invenso technology). The NORAN System 7 is a specialized energy-dispersive X-ray spectroscopy (EDS) tool used for SEM spectral imaging. Carbon tape was used to hold the sample in the system so that the weight percentage (wt. %) of the carbon was not detected during EDS. Furthermore, X-ray diffraction (XRD) patterns were also recorded for both spent catalysts and fresh catalysts (Shimadzu, XRD-6000). X-Ray generator (40 kV, 15 mA) was built with Gonimometer (Miniflex 300/600) and Detector (D/teX Ultra2). A scanning range of about 5° to 80° and a scanning speed of 3°/min were used with 1D scan mode.

The surface area and porosity analyzer (Model: ASAP 2020) were used to understand the pore structure characteristics. The adsorption and desorption isotherm data for N$_2$ gas were collected over a range of relative pressures from 0.01 to 0.99. Using the Brunauer-Emmett-Teller (BET) analysis, the specific surface area, pore volume, and average pore size were calculated. The Barrett-Joiner-Halenda (BJH) method was also used to analyze the pore size distribution. The t-plot method was used to evaluate the micropore volume ($V_{micro}$).

Example 7: Gas Analysis

An INFICON micro-GC fusion system (Model No. 074-594-P1H, USA) was used to analyze the gaseous product directly. Refinery gas checkout was used to validate the chromatography performance of micro-GC fusion during installation. The carrier gas pressure was maintained at around 58 to 60 psi in columns A and B. Before the analysis, the carrier gases were purged overnight.

Example 8: Characteristics of LDPE Feedstocks

Figure 3:
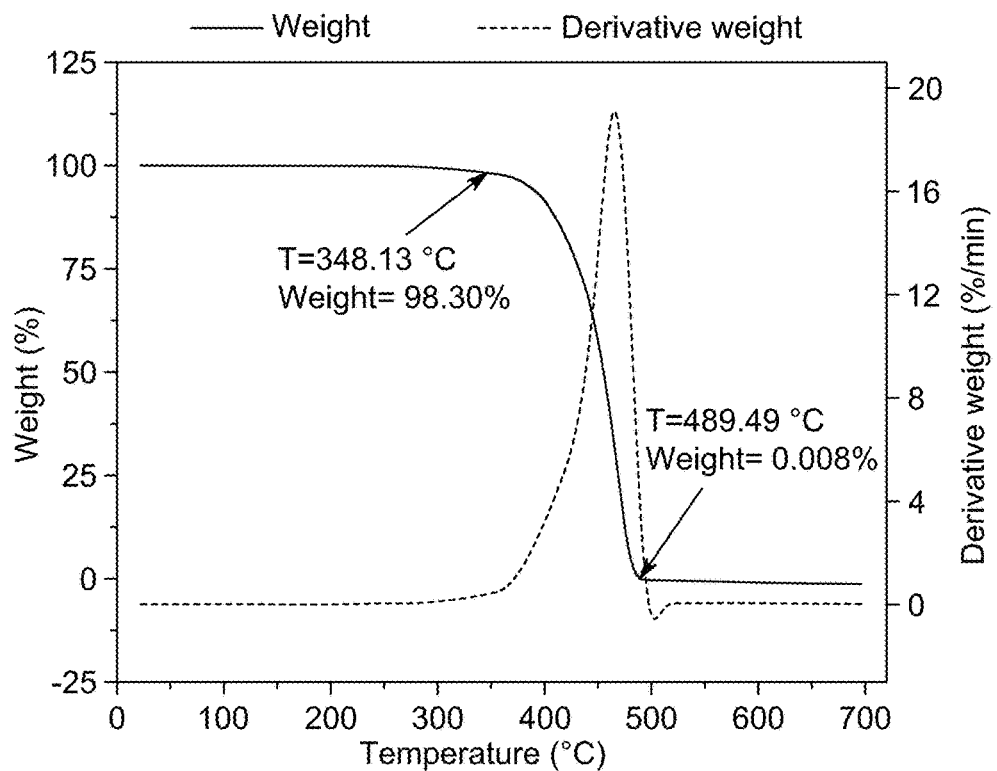
FIG. 3 shows a thermogravimetric curve of LDPE, according to certain embodiments.

TGA was employed to investigate the thermal degradation characteristics of the feedstocks, which allowed for the determination of the pyrolysis temperature. This method measures the change in weight as a function of temperature. By examining the TGA curve, the weight loss of the sample was determined with respect to the increase in temperature. FIG. 3 illustrates the TGA curve of LDPE. The mass loss in the first region (98.57° C./min to 348.01° C./min) was insignificant as it represents water and physical absorbent removal. The second region shows the highest weight loss at a temperature range of 348.01° C. to 501.33° C. All the LDPE vaporized before 500° C. Therefore, there is no weight loss after 500° C. It is also clear that there is no ash content in this sample. Consequently, the selected pyrolysis temperature for the LDPE reaction was 500° C. The derivative weight (%/min) profile provides a clearer demonstration of the weight loss behavior. A large peak between 348.01° C. to 501.33° C. temperature zone indicates mass loss of LDPE. The maximum peak position at 470° C. supports the maximum weight loss at this temperature. Then, it reduces gradually. It becomes straight after 500° C., signifying that there is no weight loss. The derivative temperature (° C./min) profile is almost straight throughout the operation. It is observed that the temperature change sharply decreases right before the second region and then immediately increases after the second region. In between these the temperature may not change in unit time. This sudden temperature change is due to phase transition and thermal decomposition of the LDPE.

Example 9: Comparative Yield Analysis

Figure 4:
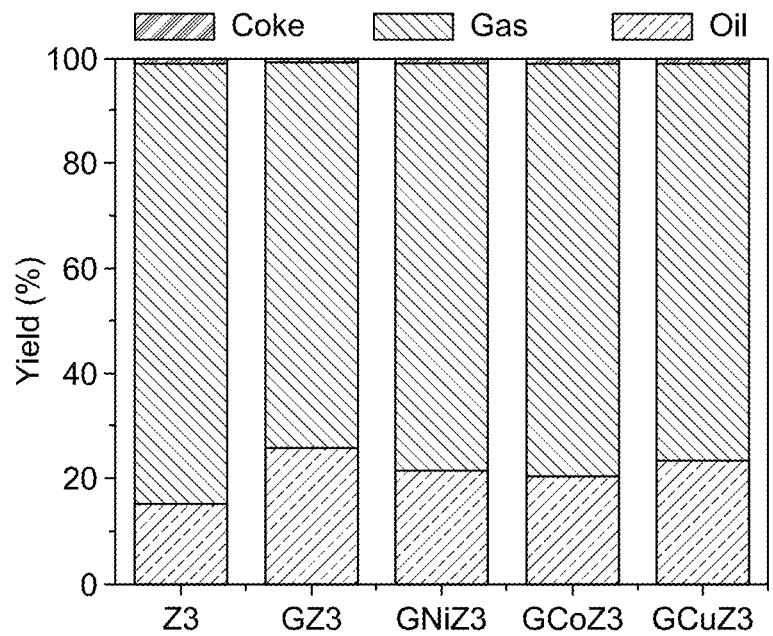
FIG. 4 illustrates percentage yield of coke, gas and oil with various catalysts, according to certain embodiments.

FIG. 4 illustrates the pyrolysis oil and gas yields obtained using different catalysts (Z3, GZ3, GNiZ3, GCoZ3, and GCuZ3). As the yield of coke was negligible, it was not shown as a product yield. Coke was mixed along with a spent catalyst. The data shows that the yield of pyrolysis oil varies between 15.33% and 26.05%, while the yield of gas varies between 73.35% and 83.87%. The SiC absorbents were utilized due to their high dielectric loss property. This phenomenon is the cause of the formation of microscopic hot spots and, as a result, the reduction in liquid yield. The yield of coke was obtained less than 1% in all cases.

Among the catalysts tested, GZ3 gives the highest yield of pyrolysis oil at around 26.05%, while Z3 gives the lowest yield at around 15.33%. On the other hand, Z3 gives the highest yield of gas at around 83.87%, while GZ3 gives the lowest yield at around 73.35%. The variation in gas and liquid yields when employing different catalysts stems from the intricacies of the pyrolysis process, which are influenced by multiple factors. The evolution of products during pyrolysis is a multifaceted sequence involving polymer material cracking, dehydrogenation, cyclization, isomerization, branching, aromatization, and various other reactions. The outcome is intricately linked to the characteristics of the catalysts used and the specific process conditions. Factors influencing product yields include acidity, basicity, redox properties, structural features, channel shapes, morphology, porosity, and more inherent to the catalysts. The heating rate, target temperature, and holding time during pyrolysis determine the resulting product distribution. Monometallic and bimetallic catalysts possess distinct properties that deviate from those of pure support materials such as ZSM-5 zeolite. The introduction of additional metals into the catalyst composition imparts specific catalytic properties related to cracking, dehydrogenation, cyclization, and aromatization. Consequently, the observed trends in product yields were attributed to the augmented cracking reactions facilitated by the presence of additional metal species in the bimetallic catalysts under the conditions of the study.

Example 10: Textual Properties ($N_2$ Sorption)

Figure 5:
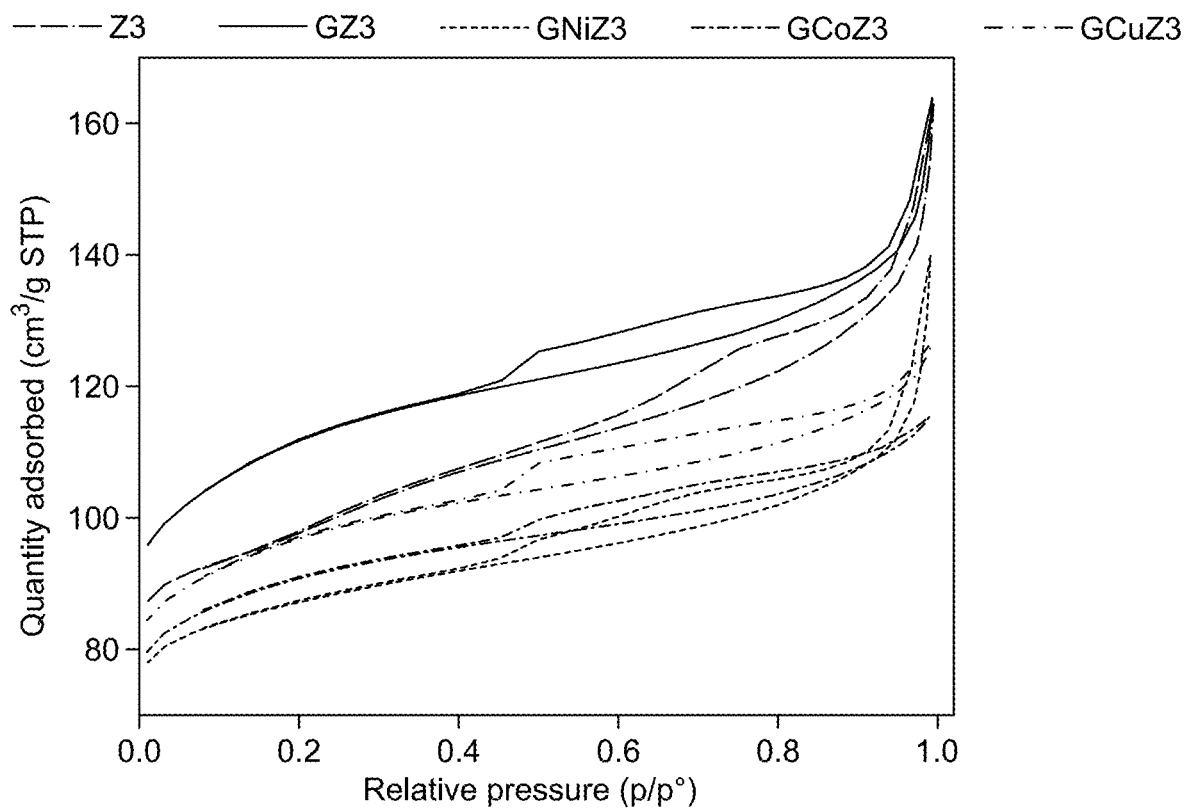
FIG. 5 is a graph illustrating nitrogen adsorption-desorption isotherms of fresh catalysts, according to certain embodiments.

Among the bi-metallic series, samples containing either Ni, Co, or Cu along with Ga were characterized in detail using $N_2$ adsorption experiments; the results are given in Table 1 and FIG. 5. As can be inferred from Table 1 and FIG. 5, the microporosity was maintained even after loading around 7% extra metal on the zeolite materials. Upon the impregnation of metals, some of the mesopores were converted to micropores, which effectively increased the surface area of the catalysts. Surface area and other parameters show a decrease upon metal addition. In addition, the samples possess a high microporosity, as seen from their micropore surface area values, which are calculated from the t-plot equation. The isotherm shape falls under type IV. However, it is a combination of both type I and type IV isotherms, as shown by the y-axis values corresponding to the p/p° values close to zero. The addition of 5% metal to the zeolite structure caused an increase in adsorbed nitrogen owing to the increase in the micropore volume and, hence, surface area as well. Furthermore, mesopores presented in the zeolite are converted to micropores due to the occupancy of Ga metal ions; whereas, when the metal contents were further increased, at least some of the micropores have been blocked, causing the loss of some fraction of the micropore volume.

$N_2$ adsorption and desorption profiles for fresh catalyst illustrate that GZ3 shows the highest quantity of nitrogen adsorption and GNiZ3 shows the minimum. When relative pressure reaches unity, the quantity adsorbed shows a sudden high value for Z3, GZ3, and GNiZ3. On the other hand, GCoZ3 and GCuZ3 show a similar pattern where the quantity adsorbed doesn't increase sharply while increasing the relative pressure. During desorption, Z3 desorption may not decrease sharply while reducing relative pressure, whereas the other four catalysts show almost the same desorption behavior, as depicted in FIG. 5.

catalyst. No diffraction peaks of Ga oxides were detected. This is due to the distribution of Ga in the large pores as fine particles, which may not be adequately crystalline to produce diffraction patterns. Intense diffraction peaks were identified at 5.82°, 6.82°, 21.1°, 21.95°, and 22.36° positions. Further, as can be seen from FIG. 7 and FIG. 8, the initial segment of the 2θ values corresponds to the JCPDS patterns for $SiO_2$ (JCPDS card no 89-1668) and $Al_2O_3$ (JCPDS card no 88-0107). Characteristic diffraction peaks of Ga, Ni, Co, and Cu were not identified, indicating high dispersion of these metals on parent zeolite.

Example 12: TGA-DSC

Figure 9:
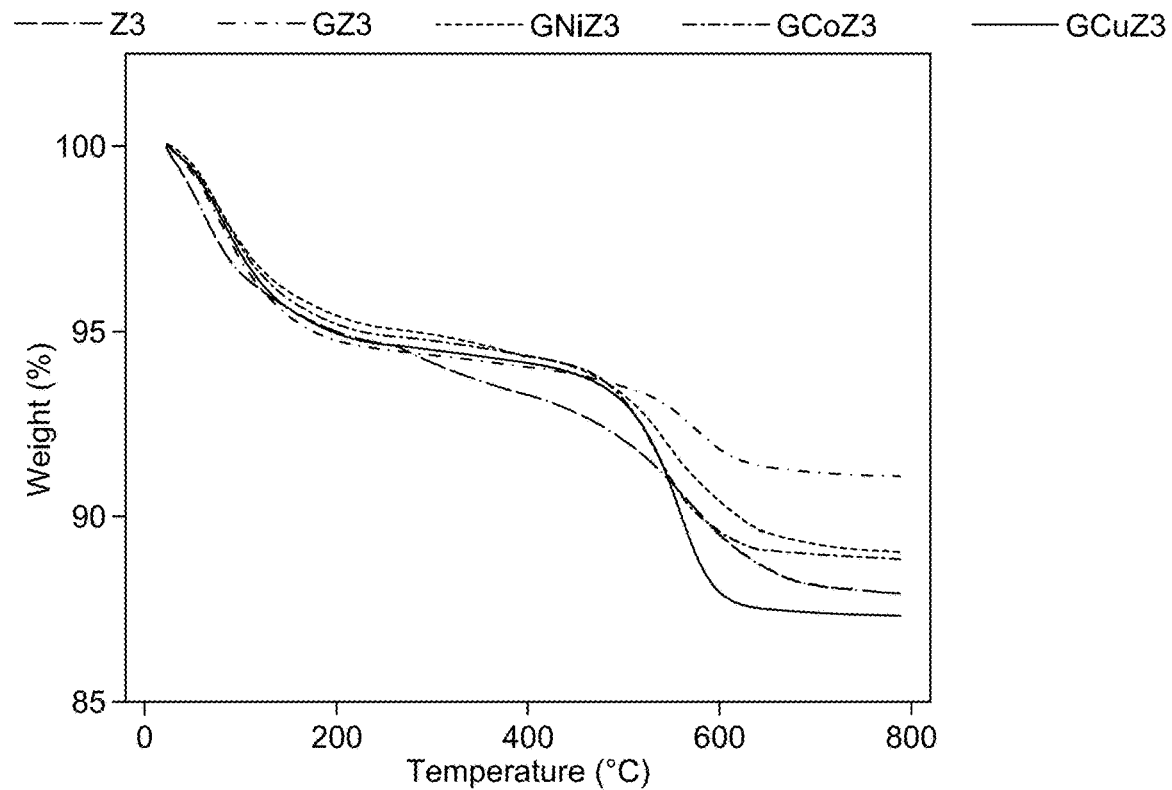
FIG. 9 illustrates thermogravimetric analysis (TGA) and weight loss percentage of spent catalysts, according to certain embodiments.
Figure 10:
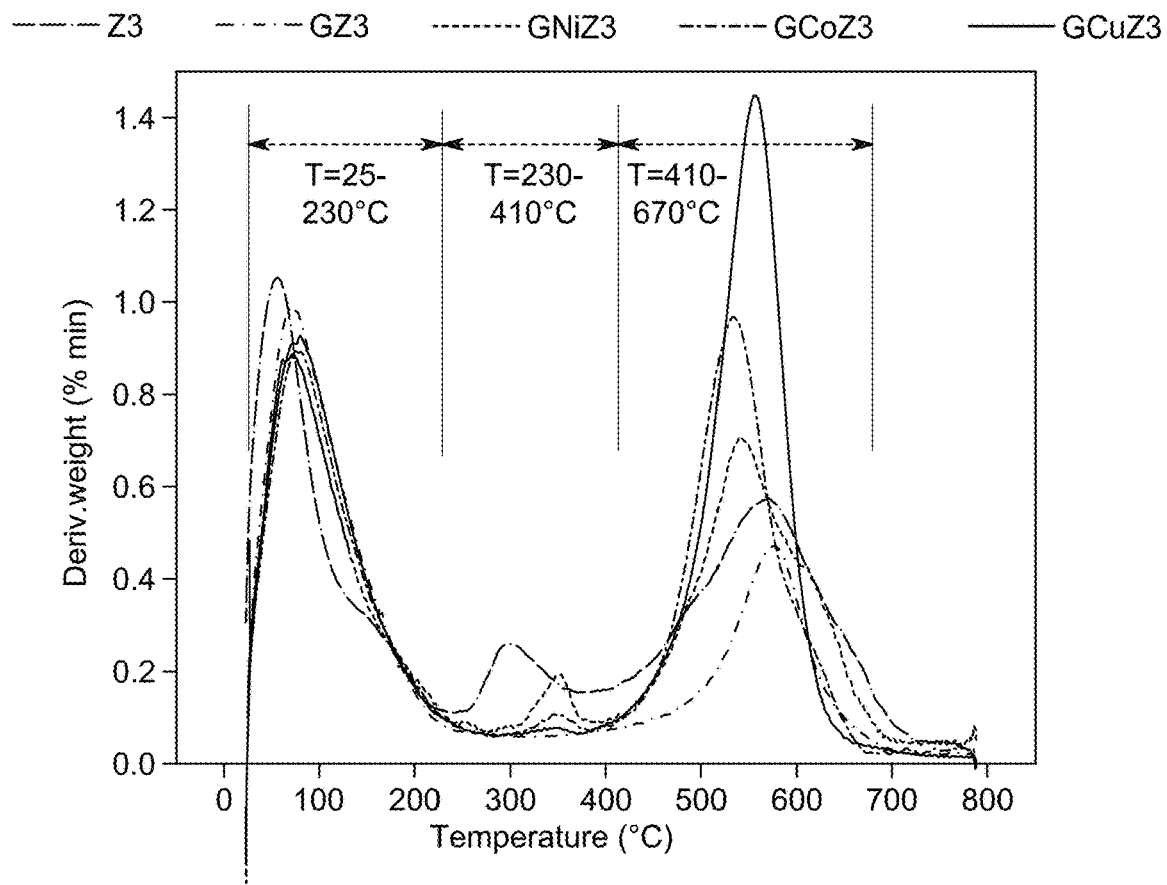
FIG. 10 illustrates TGA and weight loss percentage per minute of spent catalysts, according to certain embodiments.

FIG. 9 shows the weight loss percentage profiles, and FIG. 10 shows the derivative weight loss of the spent catalysts. FIG. 9 and FIG. 10 depict three distinct stages of mass loss. All the stages are illustrated in FIG. 10, as such, first stage T=25° C. to 230° C., second stage T=230° C. to 410° C., and third stage T=410° C. to 670° C. The first peak represents the moisture and physical absorbents released in the 25° C. to 230° C. temperature range. In the second stage, the weight loss was not very significant. The major weight loss was at the third stage and the corresponding coke was termed hard coke, whereas the soft coke was formed from the weight loss at moderate temperature. Hard coke and soft coke are byproducts formed during the process of heating and breaking down plastic materials into their constituent chemicals during pyrolysis. Hard coke, also known as fixed carbon or graphitic coke, is a solid, carbon-rich material characterized by its high carbon content and a more ordered, crystalline structure. Formation of hard coke is undesirable as it may lead to equipment fouling and reduce the overall yield of valuable pyrolysis products. Further, soft coke is a carbonaceous material that is less graphitic and more amorphous in structure compared to hard coke. It has a lower carbon content and is typically softer and less dense. Soft

TABLE 1

$N_2$ adsorption results for fresh and spent catalysts

| Parameters | Z3 Fresh | Z3 Spent | GZ3 Fresh | GZ3 Spent | GNiZ3 Fresh | GNiZ3 Spent | GCoZ3 Fresh | GCoZ3 Spent | GCuZ3 Fresh | GCuZ3 Spent |
|---|---|---|---|---|---|---|---|---|---|---|
| $S_{BET}$ | 307.3 | 222.5 | 348.5 | 262.23 | 268.5 | 215.96 | 280.7 | 218.58 | 300.5 | 229.357 |
| $S_{micro}$ | 205.6 | 174.8 | 213.7 | 195.06 | 196.9 | 160.81 | 193.7 | 173.114 | 198.3 | 180.851 |
| $S_{extr}$ | 101.2 | 47.7 | 134.8 | 67.17 | 71.6 | 55.15 | 86.9 | 45.463 | 102.2 | 48.5063 |
| $S_{des}$ | 118.1 | 43.8 | 137.4 | 48.072 | 80.99 | 38.48 | 89.9 | 29.767 | 106.8 | 30.9604 |
| $V_{micro}$ | 0.107 | 0.0924 | 0.1137 | 0.10302 | 0.103 | 0.085 | 0.1023 | 0.09135 | 0.105 | 0.09559 |
| $V_{des}$ | 0.154 | 0.103 | 0.1426 | 0.10056 | 0.118 | 0.09174 | 0.0786 | 0.07451 | 0.0938 | 0.09098 |

$S_{BET}$ = BET Surface Area, $m^2/g$;
$S_{micro}$ = t-plot Micro area, $m^2/g$;
$S_{extr}$ = t-plot External area, $m^2/g$;
$S_{des}$ = BJH Desorption area, $m^2/g$;
$V_{micro}$ = t-plot micro pore volume, $cm^3/g$;
$V_{des}$ = BJH Des. pore volume, $cm^3/g$.

Figure 6A:
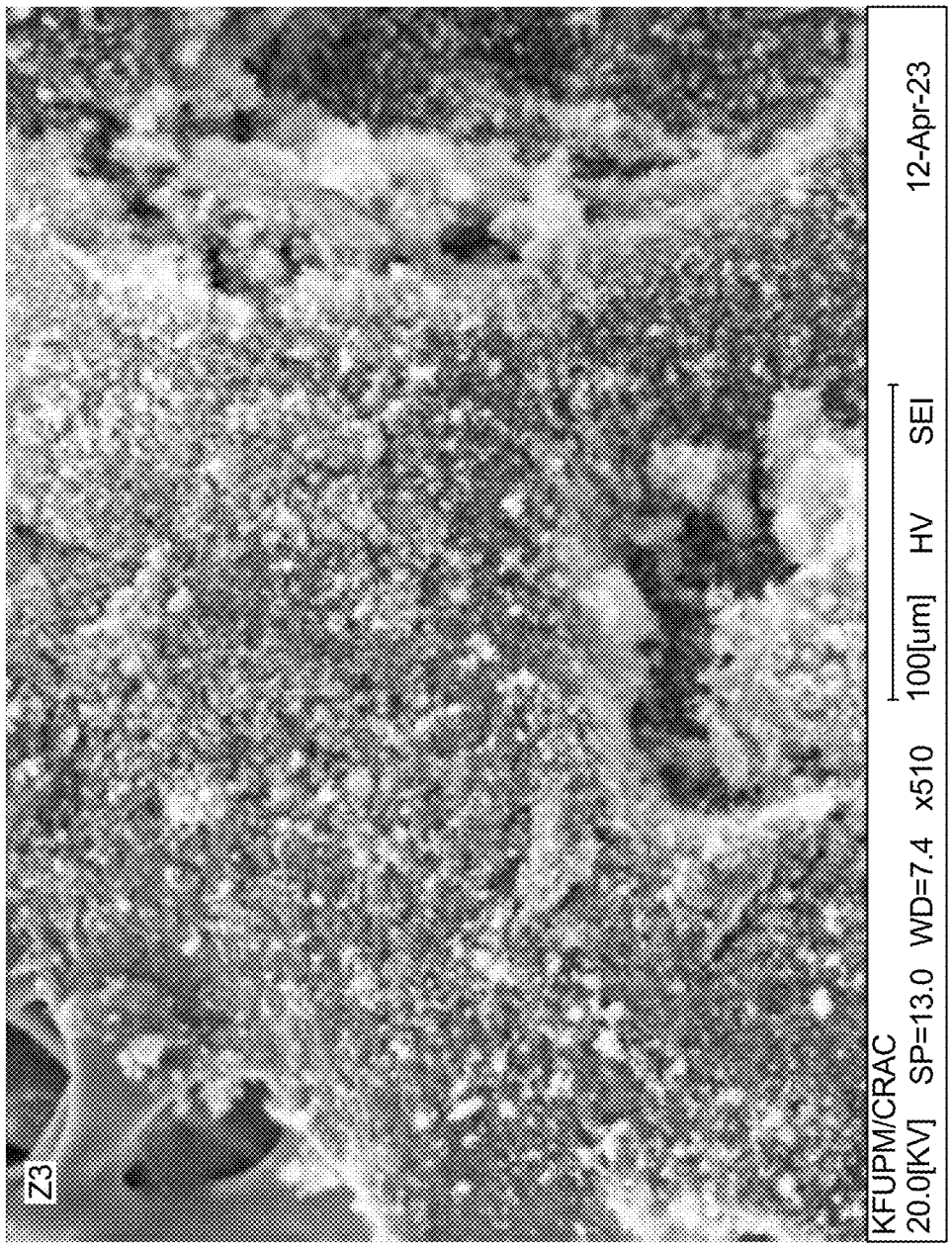
FIG. 6A is a scanning electron microscopy (SEM) image of a Z3 spent catalyst, according to certain embodiments.
Figure 6B:
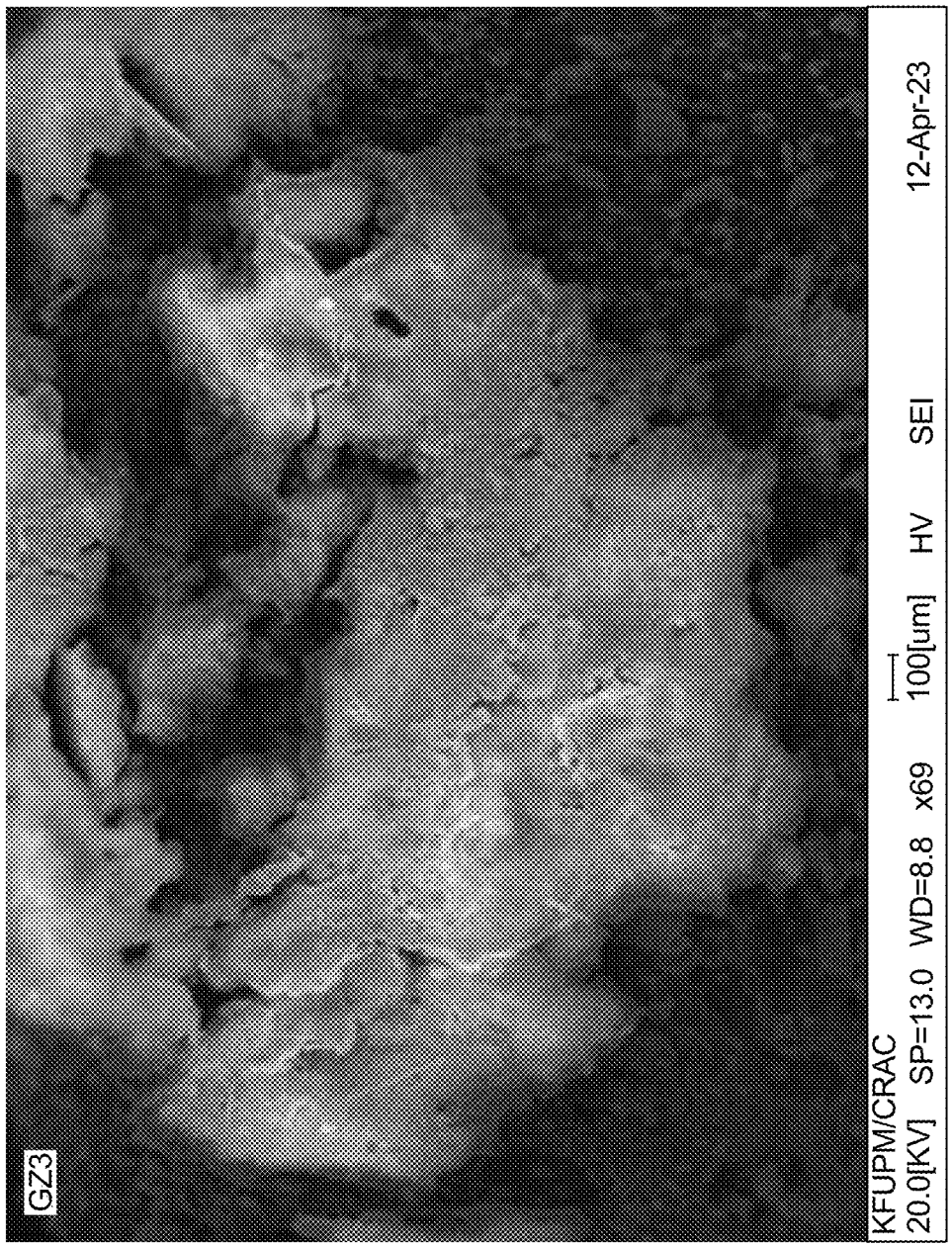
FIG. 6B is a SEM image of a GZ3 spent catalyst, according to certain embodiments.
Figure 6C:
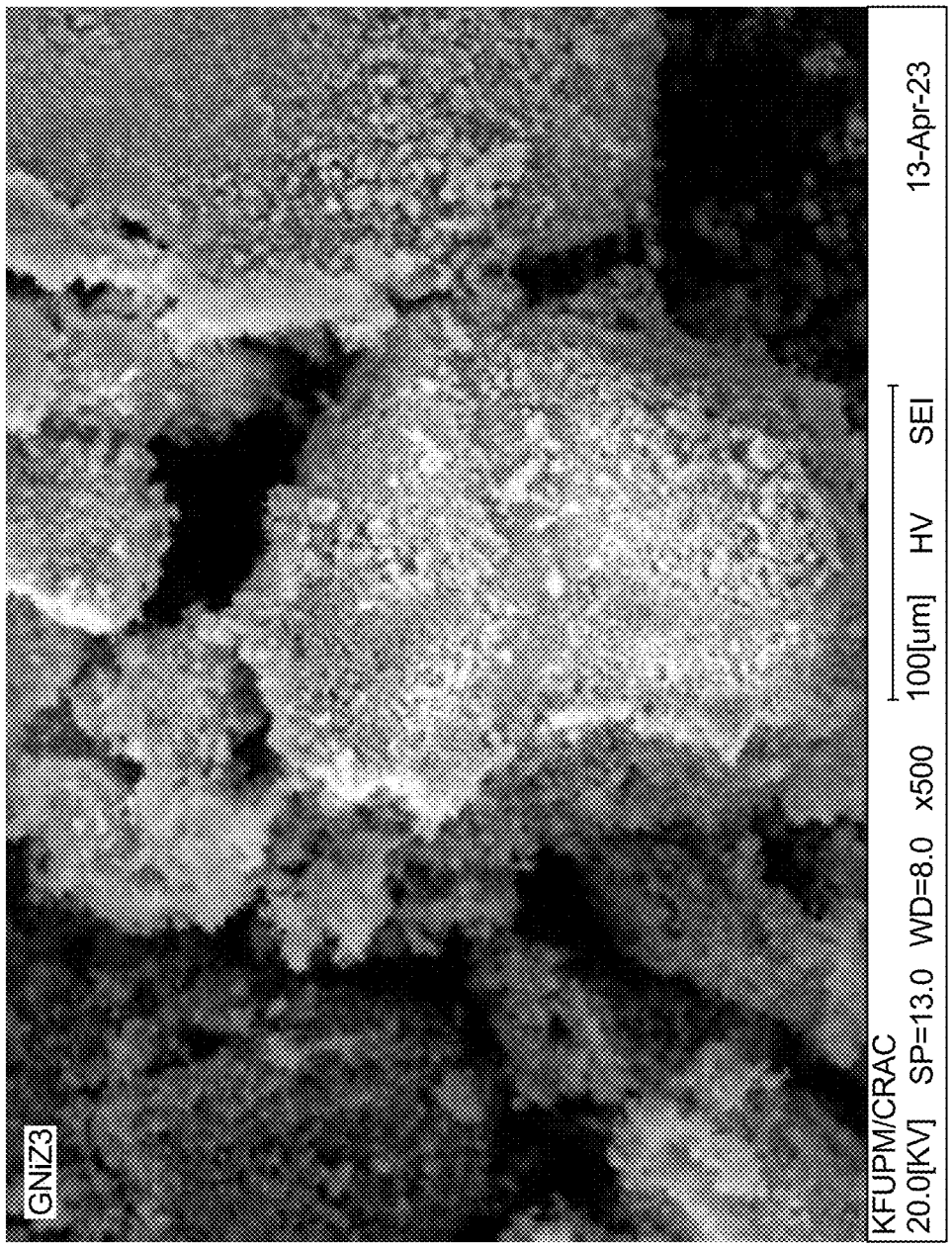
FIG. 6C is a SEM image of a GNiZ3 spent catalyst, according to certain embodiments.
Figure 6D:
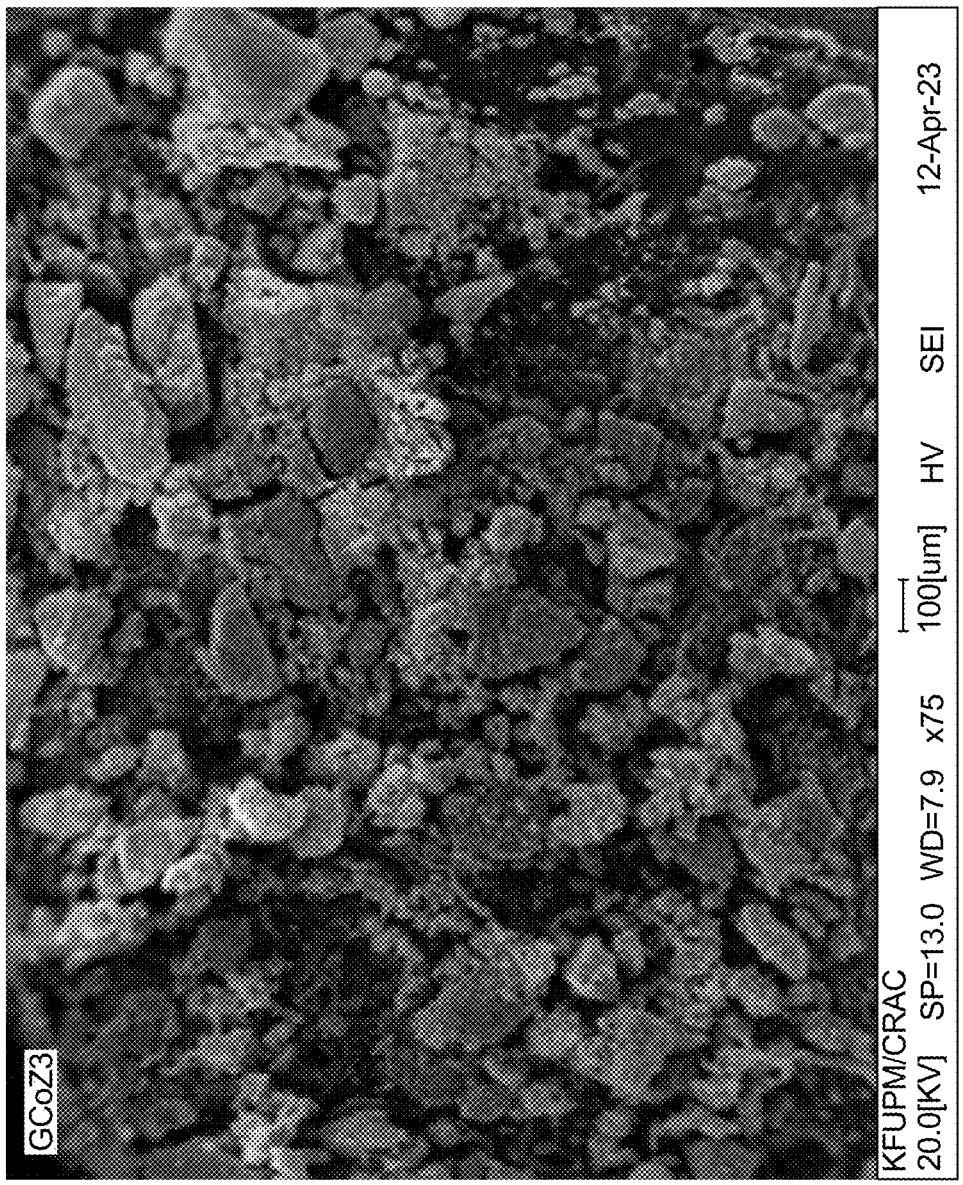
FIG. 6D is a SEM image of a GCoZ3 spent catalyst, according to certain embodiments.
Figure 6E:
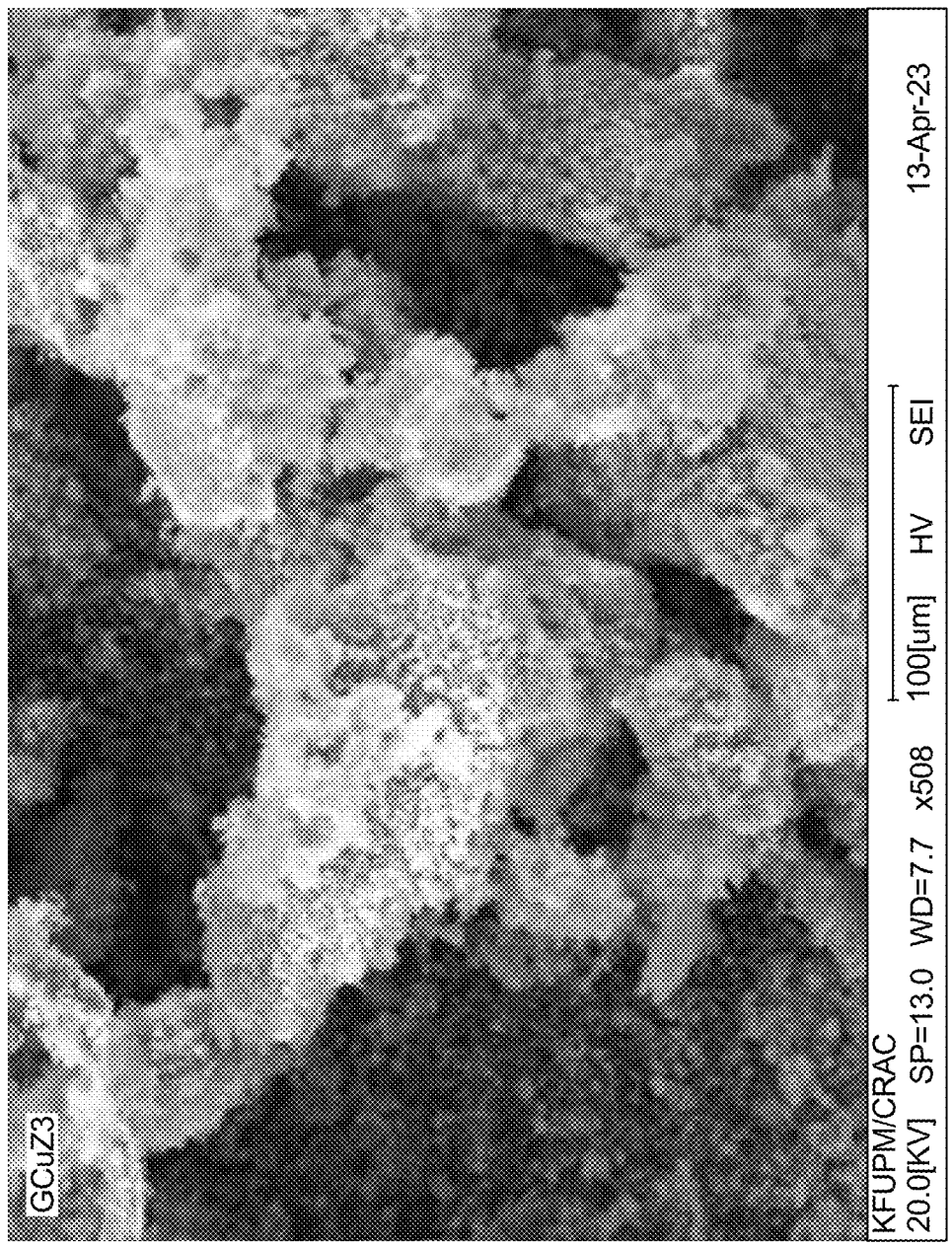
FIG. 6E is a SEM image of a GCuZ3 spent catalyst, according to certain embodiments.
Figure 6F:
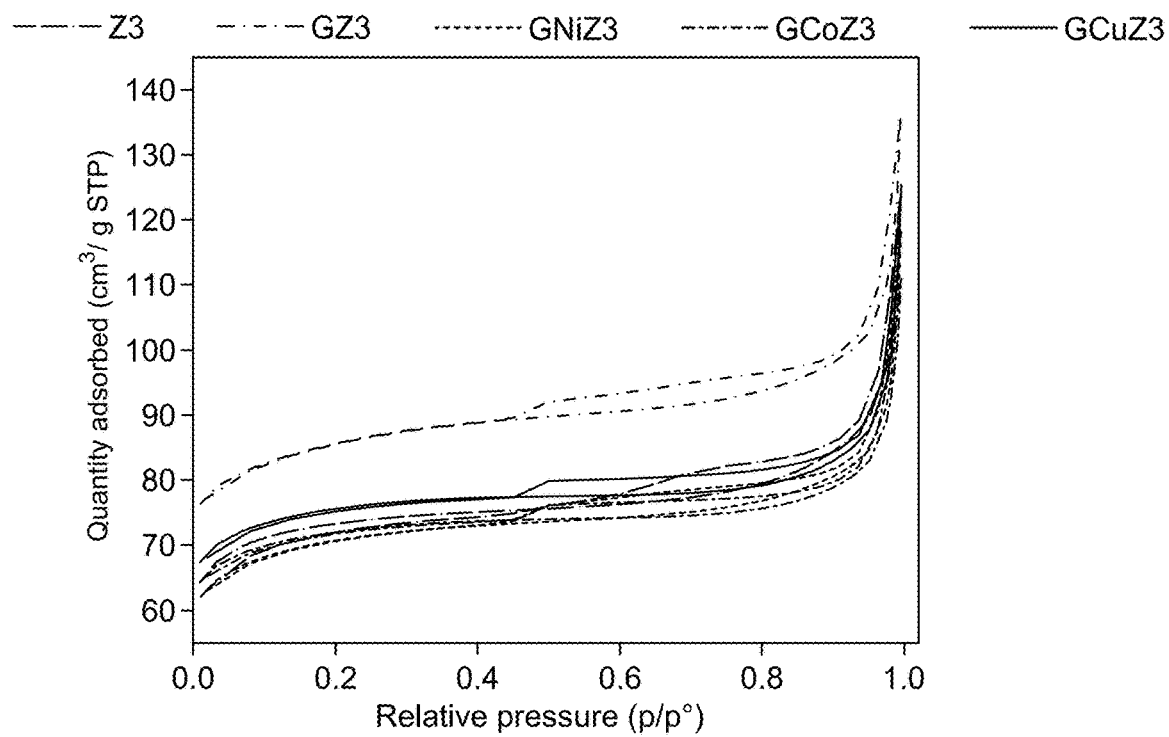
FIG. 6F is a graph of $N_2$ adsorption-desorption isotherms of spent catalysts, according to certain embodiments.

For the spent catalyst, $N_2$ adsorption and desorption isotherms for GZ3 demonstrate the highest quantity of nitrogen adsorption. The other four catalyst profiles have almost the same quantity adsorption and desorption trend, as depicted in FIG. 6F.

Example 11: Crystal Phase (XRD)

Figure 7:
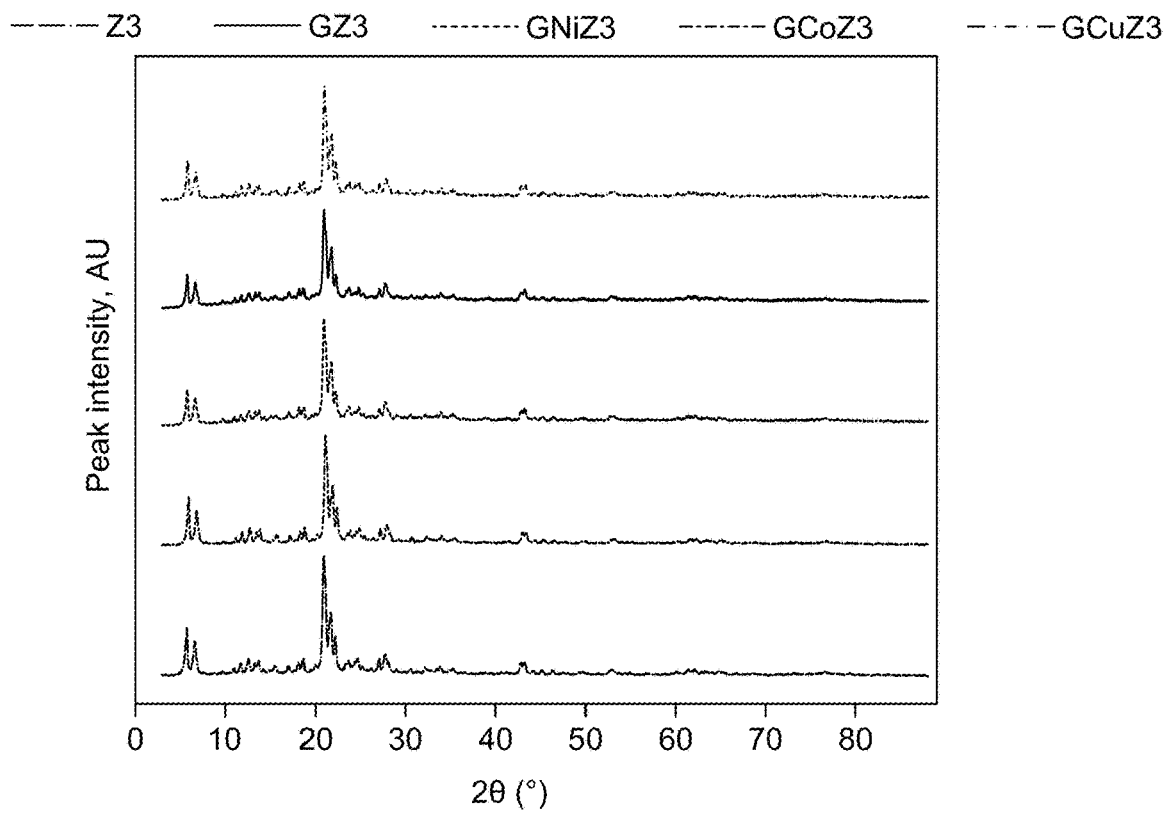
FIG. 7 shows X-ray diffraction patterns (XRD) of fresh catalyst samples, according to certain embodiments.
Figure 8:
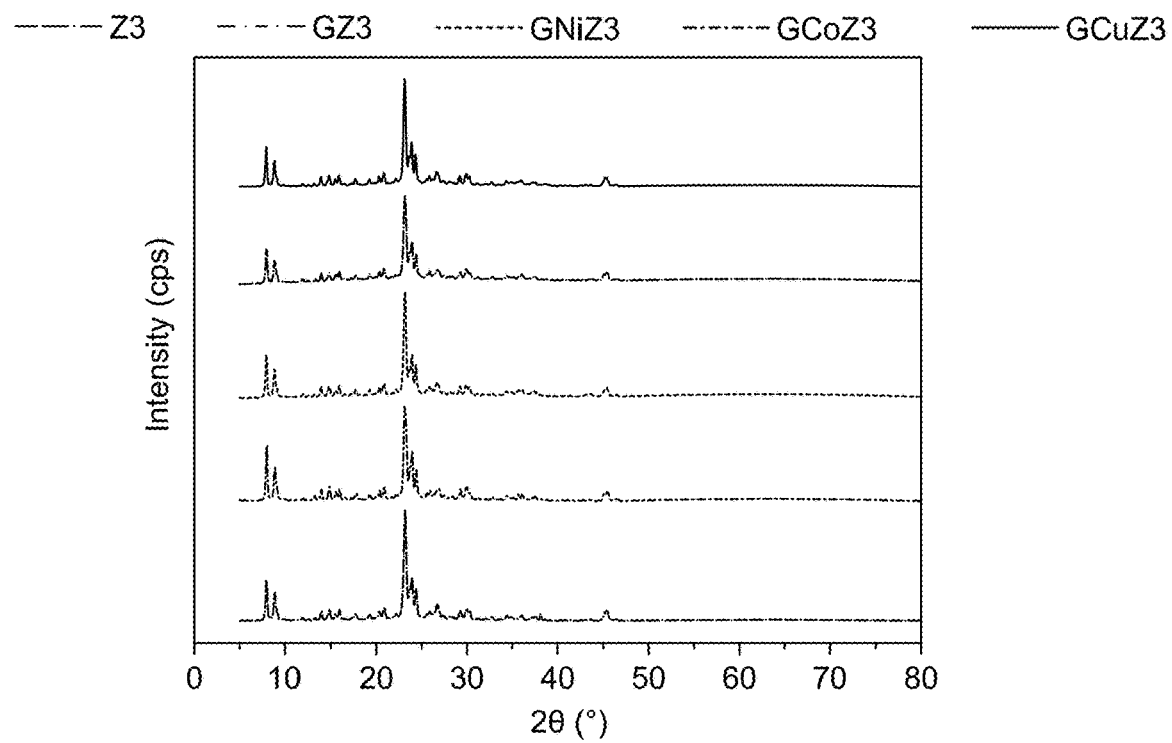
FIG. 8 shows XRD patterns of spent catalysts, according to certain embodiments.

FIG. 7 illustrates the diffraction patterns for fresh bimetallic samples containing one metal out of Ni, Co, and Cu along with Ga. FIG. 8 depicts the XRD patterns of the spent coke is often considered a lower-value byproduct of pyrolysis compared to hard coke. It can result from incomplete pyrolysis or cracking of the plastic feedstock and may contain a mixture of carbon and various volatile compounds.

GCuZ3 catalyst contains the maximum amount of coke, whereas GZ3 contains the minimum. The other three catalysts follow the following sequence: Z3>GCoZ3>GNiZ3. As mentioned above, aromatic hydrocarbon content in pyrolysis oil was highest, and hydrogen release was maximum for GCuZ3. Hence, the maximum amount of coke was deposited on GCuZ3 during the reaction. Moreover, the Z3 catalyst has high acidic values, hosting surplus primary and secondary cracking reactions. Due to the absence of other metals to perform reactions, coke formation is highest in this sample.

Example 13: Morphology (SEM-EDS)

The morphology of the coke on the spent catalysts was examined by SEM analysis. SEM of fresh catalysts was also performed to understand the change after pyrolysis. Along with SEM, EDS was also accomplished both for fresh and spent catalysts to determine the elemental composition of the samples. SEM-EDS results for both the spent and the fresh catalysts are illustrated in FIGS. 6A-6E and FIGS. 12A-12E, respectively. The color of all spent catalysts was black after pyrolysis, indicative of coke deposition and deactivation.

Figure 13:
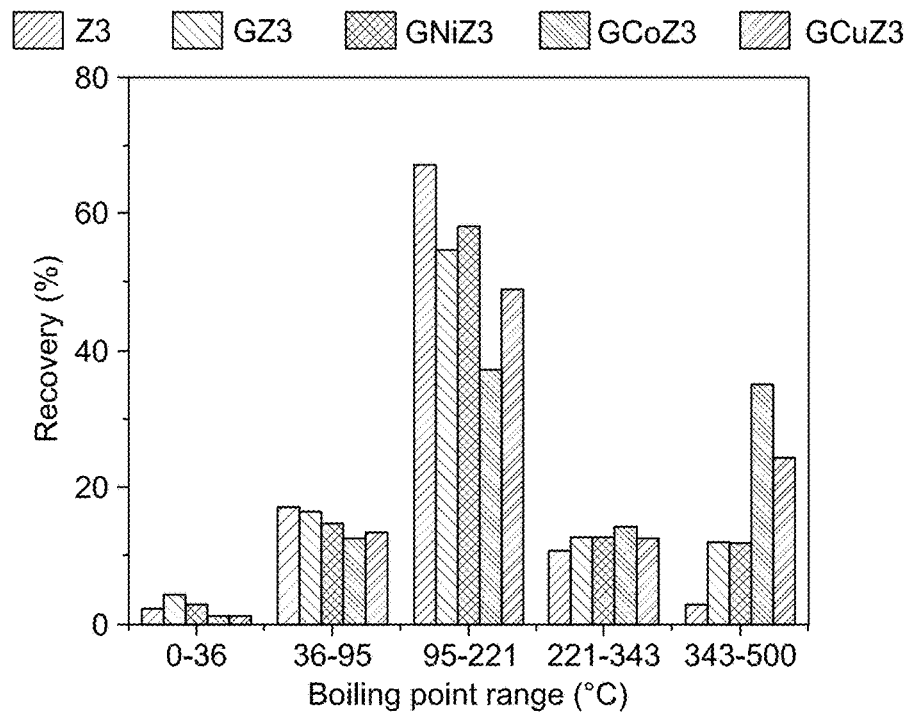
FIG. 13 is a graph depicting recovery percentage versus boiling point range of pyrolysis oil using SimDist analysis, according to certain embodiments.

The morphologies of Z3, Ga-doped Z3, Ni/Co/Cu incorporation, along with Ga-doped Z3 are almost similar. These similar images show that the metal incorporation does not affect the crystallinity of the parent HZSM-5, supporting the XRD results. However, metal doping shows high agglomeration compared to parent zeolite. On the other hand, mesopores that provide large surface area and volume for chemical reactions cannot be distinguished from SEM as the size of the mesopore varies from 2 nanometers (nm) to 50 nm, where SEM images were taken with 100 micrometers (μm) magnification. Disordered meso-porosity may form both inside and surrounding zeolite crystals due to the clustering of small crystals of varying sizes that make up zeolite particles. The presence of visibly rough outer surfaces indicates an increase in defect sites for the spent catalyst. EDS result indicates that for fresh catalysts, Z3 contains almost no metal except Si (34.83 wt. %) and Al (3.45 wt. %). The Ga weight percentage in GZ3 was found to be 3.75%. Incorporating Ni, Co, and Cu metals in GZ3 was found valid through EDS. Table 2 shows the elemental composition analysis in detail in weight percentage units. The findings agree with the notion that zeolite Z3 is the source of aluminum oxide and silicon oxide, onto which successful impregnation of Ga, Ni, Co, and Cu was performed.

pyrolysis oil fractions can be observed by analyzing Table 3 and referring to the SimDist plot shown in FIG. 13.

TABLE 3

Different fractions of pyrolysis oil using different catalysts

| Catalyst name | Naphtha (%) | Middle Distillate (%) | Heavy Cycle Oil (%) |
|---|---|---|---|
| Z3 | 86.4 | 10.8 | 2.8 |
| GZ3 | 75.4 | 12.6 | 11.9 |
| GNiZ3 | 75.7 | 12.6 | 11.7 |
| GCoZ3 | 50.7 | 14.1 | 35.2 |
| GCuZ3 | 63.3 | 12.3 | 24.4 |

To assess the suitability of the produced pyrolysis oil as a potential refinery stream, the simulated distillation curves of vacuum gas oil (VGO) and light cycle oil (LCO) were compared, which are conventional streams used in refineries. The results indicate that the pyrolysis oils, with a final boiling point of around 500° C., may be considered valuable feedstock for catalytic cracking or hydrocracking units combined with VGO or LCO, respectively. Generally, a pyrolysis oil must possess a moderate fraction of naphtha and a high concentration of middle distillates, minimizing excessive gas production.

As can be seen from Table 3 and FIG. 13, the pyrolysis oil produced using the GCoZ3 catalyst may be co-fed with VGO to the fluid catalytic cracking (FCC) unit due to the similarity in their distillation curves. On the other hand, the pyrolysis oil obtained using other catalysts is deemed suitable for blending with LCO and feeding into a hydroprocessing unit. The pyrolysis oil produced with GCuZ3 may also be used as feedstock for petrochemical applications due to its high aromatic content, as evidenced by the GC-MS data.

Example 15: GC-MS Analysis

GC-MS is an analytical technique used to identify and quantify the chemical composition of complex mixtures like pyrolysis oil. The GC-MS spectrum of pyrolysis oil shows

TABLE 2

Elemental composition analysis of fresh and spent catalysts by EDS

| | Z3 | | GZ3 | | GNiZ3 | | GCoZ3 | | GCuZ3 | |
|---|---|---|---|---|---|---|---|---|---|---|
| Element | Fresh | Spent | Fresh | Spent | Fresh | Spent | Fresh | Spent | Fresh | Spent |
| O | 60.6 | 57 | 59.86 | 58.95 | 54.49 | 55.54 | 61.5 | 63.64 | 54.58 | 55.72 |
| Si | 34.83 | 32.93 | 33.82 | 34.03 | 34.59 | 31.91 | 29.71 | 28.04 | 34.62 | 32.18 |
| Al | 3.45 | 2.1 | 2.34 | 2.14 | 1.94 | 2.52 | 1.97 | 2.34 | 2.14 | 2.12 |
| Ga | — | — | 3.75 | 4.15 | 4.8 | 5.72 | 4.32 | 4.22 | 3.36 | 3.47 |
| Ni | — | — | — | — | 3.94 | 3.64 | — | — | — | — |
| Co | — | — | — | — | — | — | 2.23 | 1.47 | — | — |
| Cu | — | — | — | — | — | — | — | — | 2.45 | 1.82 |

All the values of the parameters were expressed in wt. %.

Example 14: Simulated Distillation (SimDist) Analysis

Figure 14:
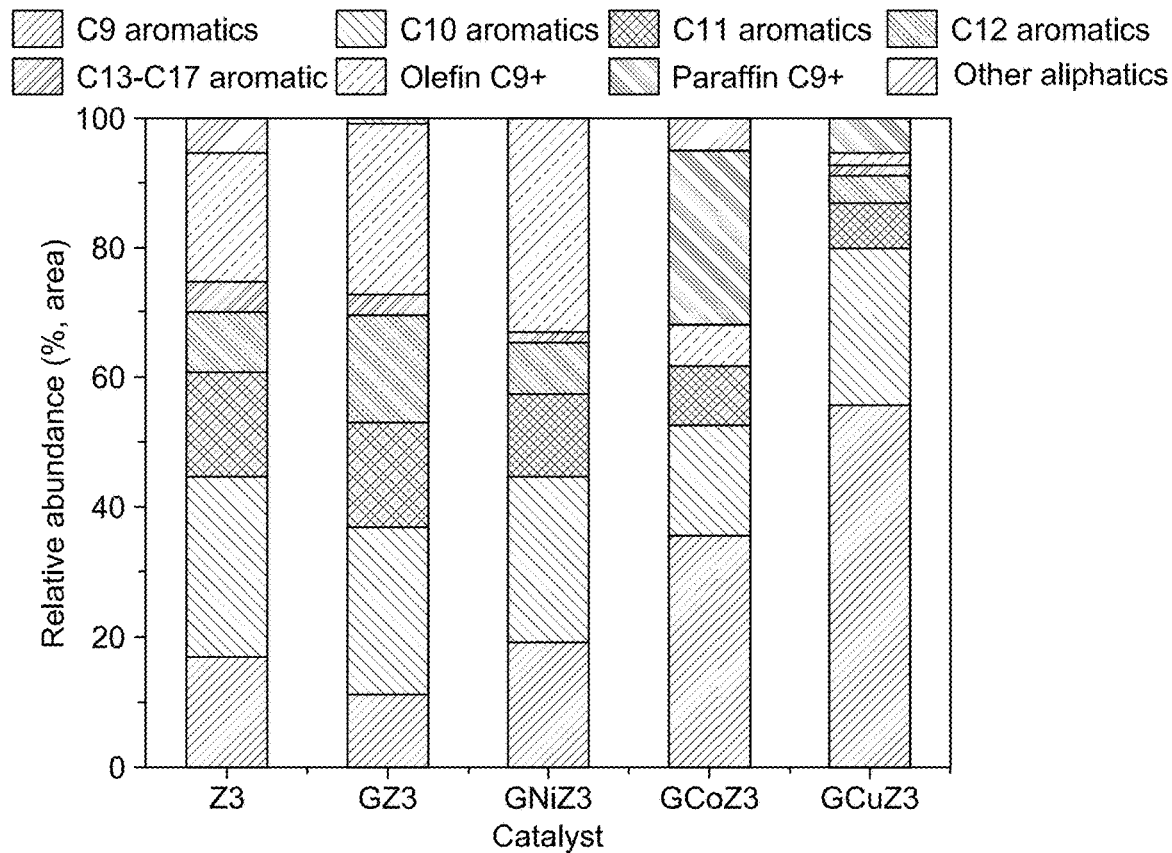
FIG. 14 depicts gas chromatography-mass spectrometry (GC-MS) analysis of pyrolysis oils, according to certain embodiments.

Simulated distillation analysis allowed for its categorization into three distinct fractions based on boiling point temperature (TB) criteria. These fractions were identified as naphtha (TB below 216° C.), middle distillates (TB ranging from 213° C. to 343° C.), and heavy cycle oil (TB above 343° C.). The impact of catalyst choice on the distribution of that aromatics were the main products. The formation of C9 aromatics was the minimum for GZ3, which was 11%. GCuZ3 resulted in the maximum C9 aromatics conversion, which was almost 55% of the total product yield. As can be seen from FIG. 14, GNiZ3 and GCoZ3 showed 19% and 35% C9 aromatic conversion, respectively. C9 aromatics are mainly benzene derivatives.

Pyrolysis oil contains around 90% of C9-C12 aromatics while using GCuZ3, which could be used as a feedstock for producing various chemicals, including benzene, toluene, xylene, and other heavier aromatic compounds. These compounds are important building blocks to produce plastics, synthetic fibers, and other materials. In general, the octane number in a fuel maintains the following sequence, monocyclic aromatic hydrocarbons (MAHs)>polycyclic aromatic hydrocarbons (PAHs)>iso-aliphatics >cyclo-aliphatics >n-aliphatics. The presence of high levels of aromatics, specifically MAHs, when using GCuZ3 indicates a high-octane number. This indicates that the oil derived from GCuZ3 can be blended with other pyrolyzed oils to enhance their ignition quality.

The mechanism of the reaction begins with breaking the large molecules by catalysts into smaller hydrocarbon fragments, creating a "hydrocarbon pool". In general, polymethylbenzene, benzenium cations, carbenium ions, or naphthenes may all exist in the hydrocarbon pool in a state of pseudo-equilibrium. Further, naphthalenes and other polycyclic aromatics are produced by the interaction of monocyclic aromatics with other oxygenates. Acidic catalysts prefer to crack olefins rather than dehydrogenate olefins like the zeolites utilized in the present disclosure. To encourage the formation of olefin and aromatic compounds, a second functionality (in addition to cyclo-oligomerization) is also required. Furthermore, dehydrogenating metals give acidic catalysts, like zeolites with high Bronsted acid functionality (owing to the presence of protons), such as Lewis acid functionality. Moreover, metal impregnation can enhance functionalities like dehydrogenation, isomerization, and cyclization; the selectivity shifted to aromatics, and the quantity of produced aliphatics decreased.

Co may promote specific catalytic pathways that favor the production of aliphatic hydrocarbons or other non-aromatic compounds over aromatics. This selectivity may result in a lower overall aromatic content in the oil. Co may act as a hydrogenation catalyst, promoting the saturation of double bonds and the conversion of aromatics to aliphatic compounds. This process may reduce the concentration of aromatics in the oil. The presence of acidity sites on the catalyst may also influence the product distribution.

The ability of the GCuZ3 catalyst to produce most C9 aromatics is attributed to a plurality of factors. Cu, present in the catalyst, possesses catalytic activity that promotes the formation of aromatic compounds through various reactions, including cyclization and aromatization. This contributes to the selective conversion of precursor compounds into C9 aromatics. The combination of Ga and Cu in the GCuZ3 catalyst also leads to synergistic effects that enhance the aromatization of hydrocarbons, resulting in a higher yield of C9 aromatics.

Example 16: $^1$H-NMR Analysis

The 1H-NMR spectra provide information about the chemical composition of a sample in terms of the hydrogen types present in the sample, with the x-axis representing the chemical shift and the y-axis representing the signal intensity. Chemical shift refers to the resonant frequency of a nucleus in a magnetic field, typically within the range of 0 parts per million (ppm) to 12 ppm for $^1$H-NMR spectra. In complex mixtures like pyrolysis oil and gasoline, peaks may overlap, so a specified range is used to determine the occurrence of functional groups.

Figure 15:
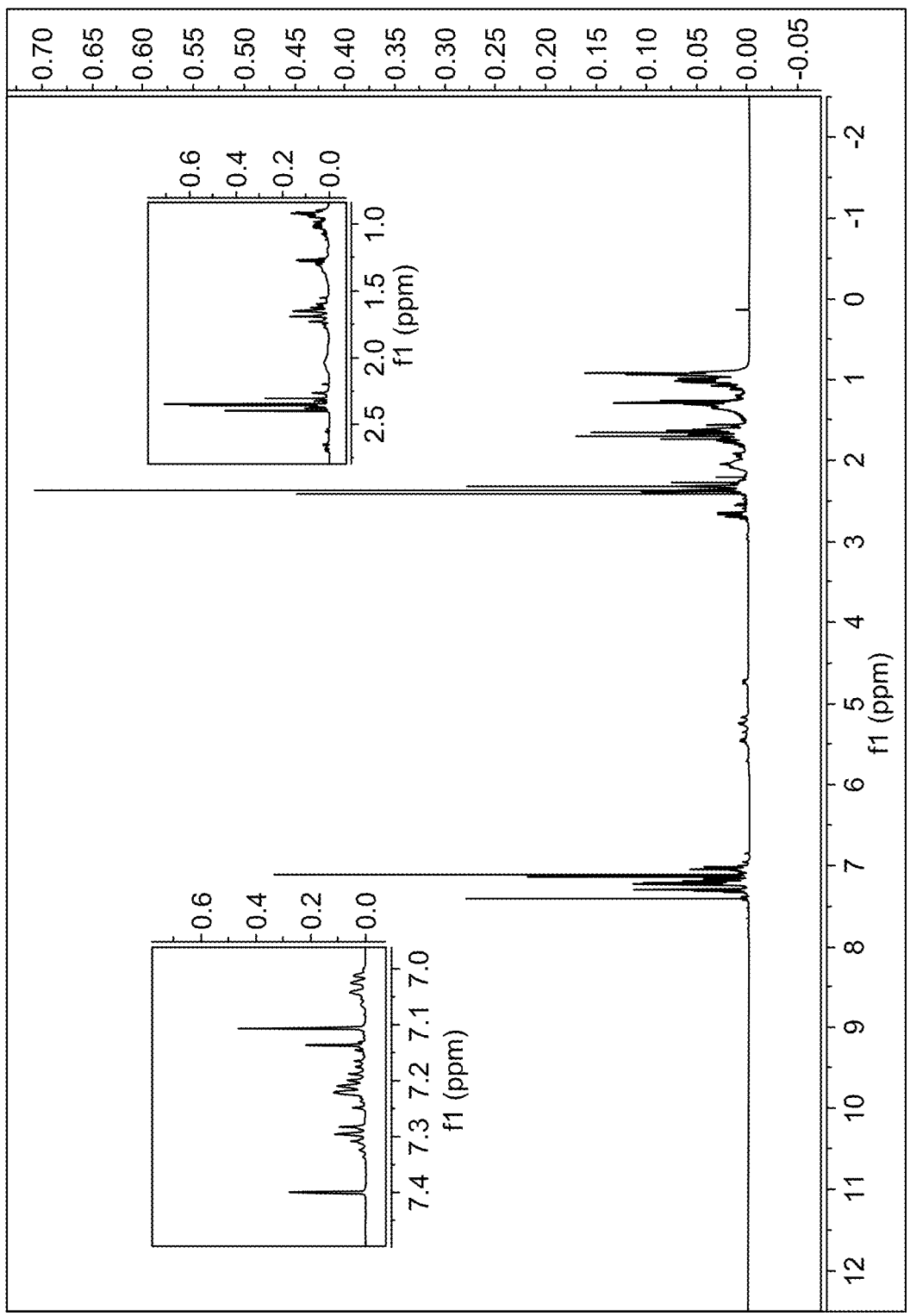
FIG. 15 depicts a nuclear magnetic resonance analysis ($^1$HNMR) spectrum of Z3 catalytic pyrolysis derived oil, according to certain embodiments.
Figure 16:
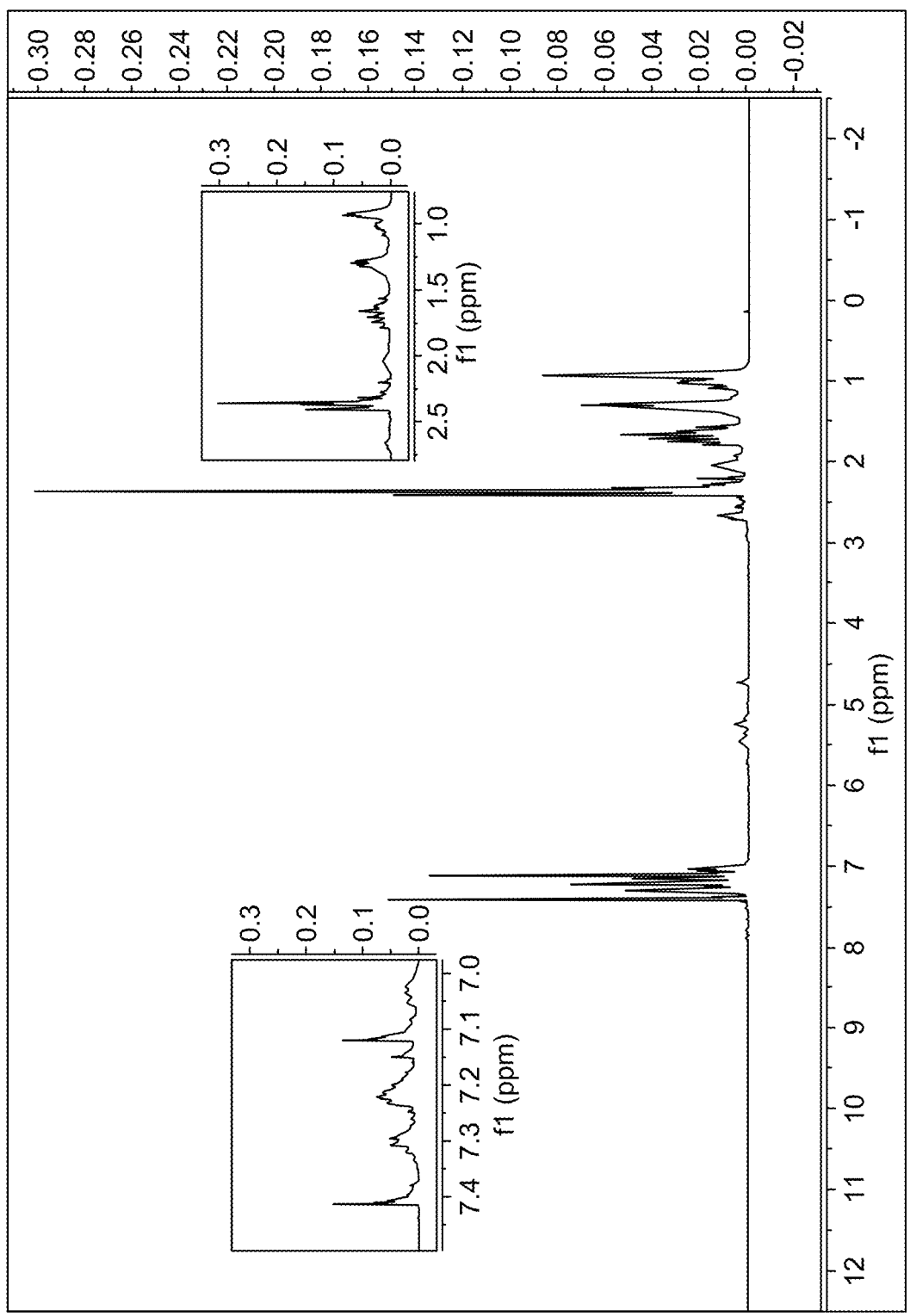
FIG. 16 depicts a $^1$HNMR spectrum of GZ3 catalytic pyrolysis derived oil, according to certain embodiments.

FIG. 15 and FIG. 16 depict the $^1$HNMR spectra for Z3 & GZ3 catalytic pyrolysis derived oil, respectively. The spectral line proves the presence of aromatic H, paraffinic CH$_3$ group in the alpha position to the aromatic ring, paraffinic CH$_2$ group in the alpha position to the aromatic ring, and naphthenic CH groups in the pyrolysis oil. Peaks in the region between 6.2 ppm and 7.4 ppm indicate the high percentages of aromatic chemical classes in the obtained pyrolysis oil. These aromatics were also found in GC-MS. Therefore, 1H-NMR data is aligned with GC-MS data.

Example 17: FTIR Analysis

Figure 11:
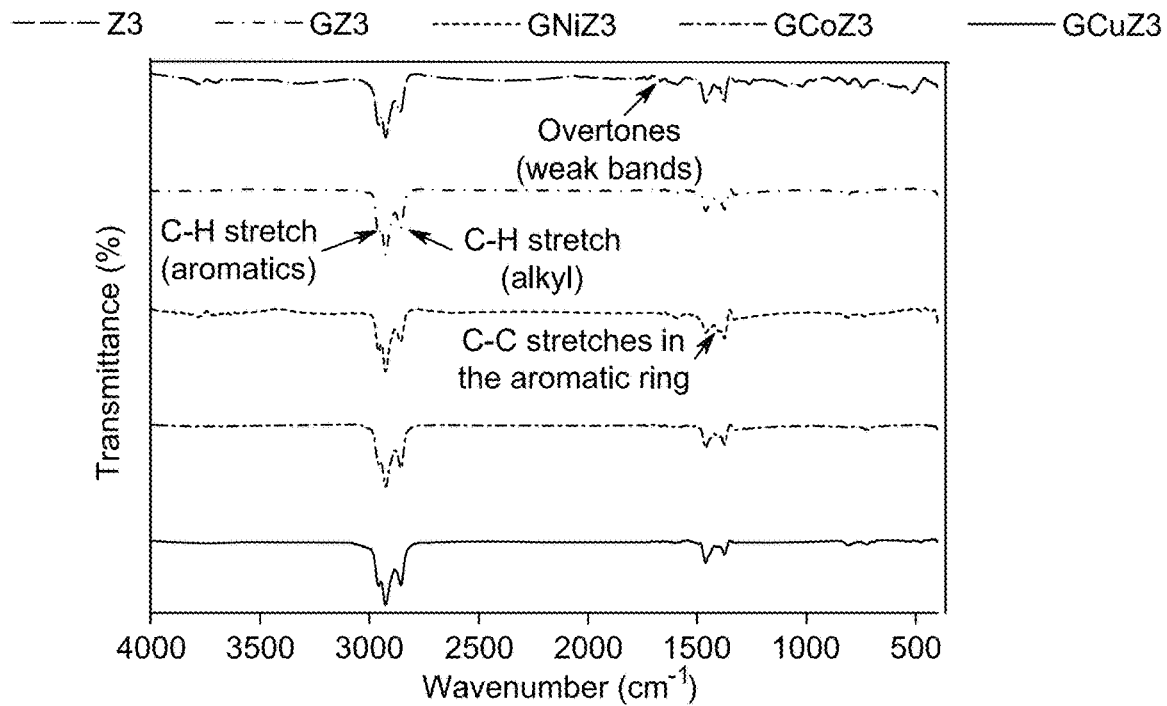
FIG. 11 illustrates Fourier transform infrared (FTIR) spectra of pyrolysis oil samples, according to certain embodiments.
Figure 12A:
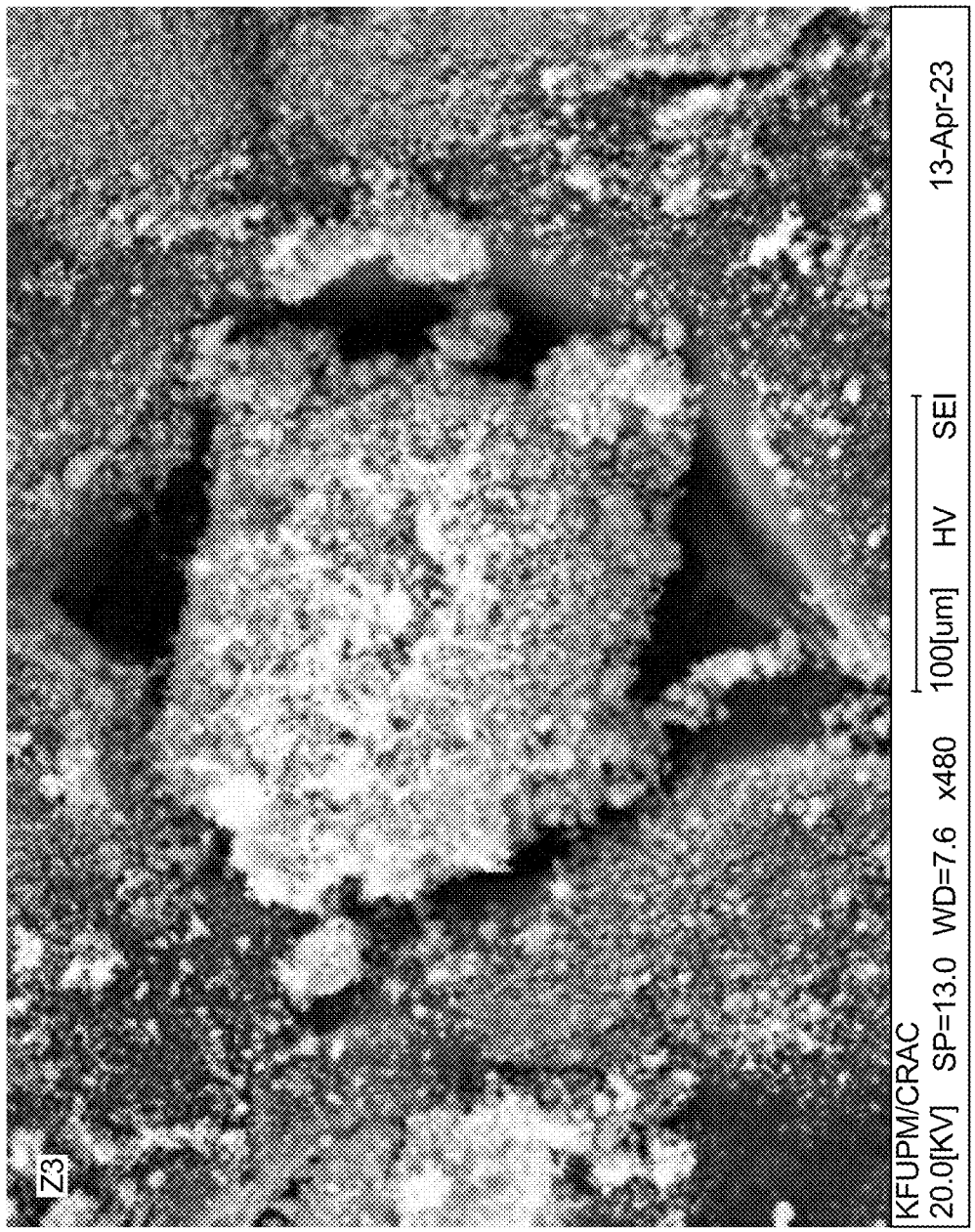
FIG. 12A is a SEM image of a Z3 fresh catalyst, according to certain embodiments.
Figure 12B:
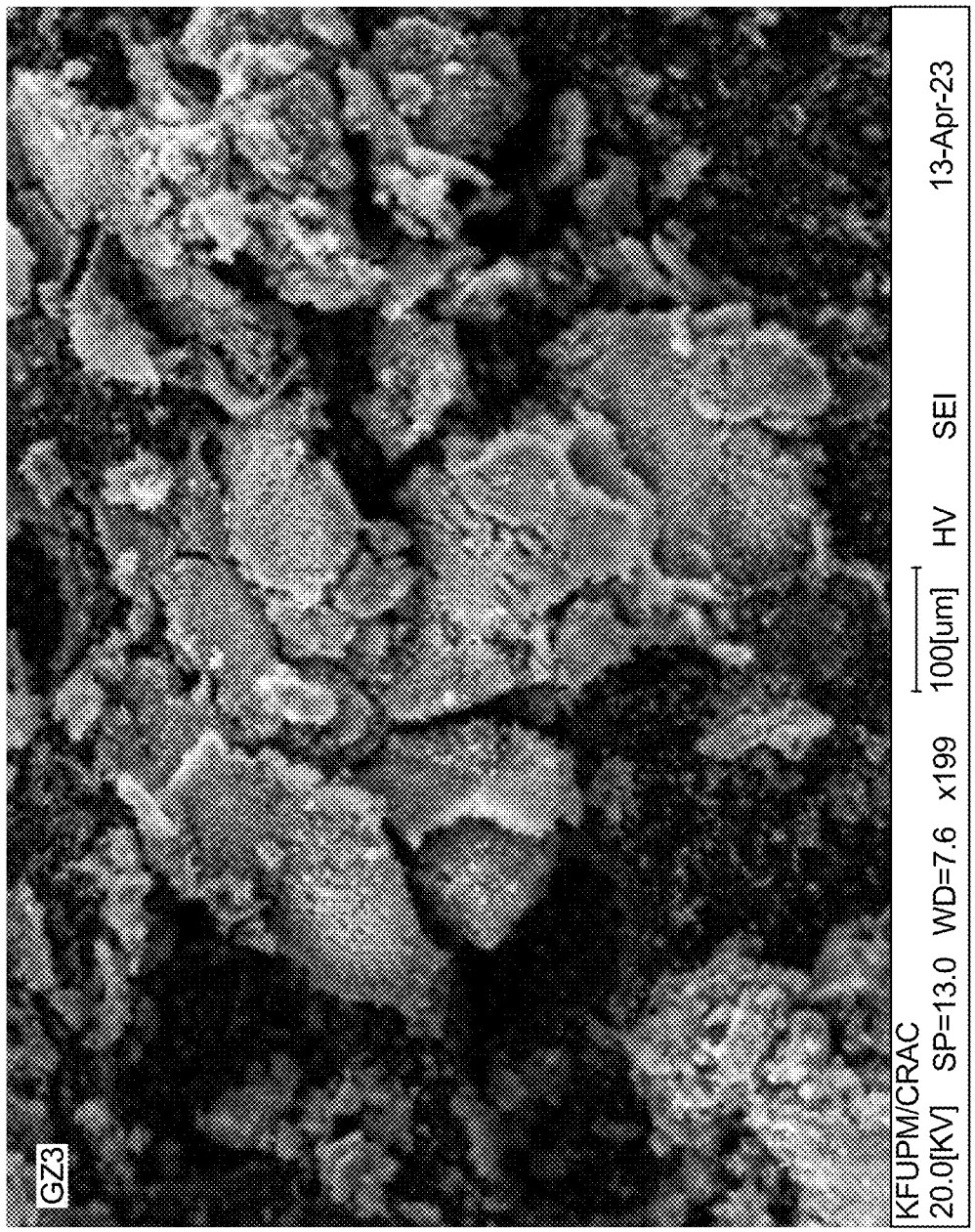
FIG. 12B is a SEM image of a GZ3 fresh catalyst, according to certain embodiments.
Figure 12C:
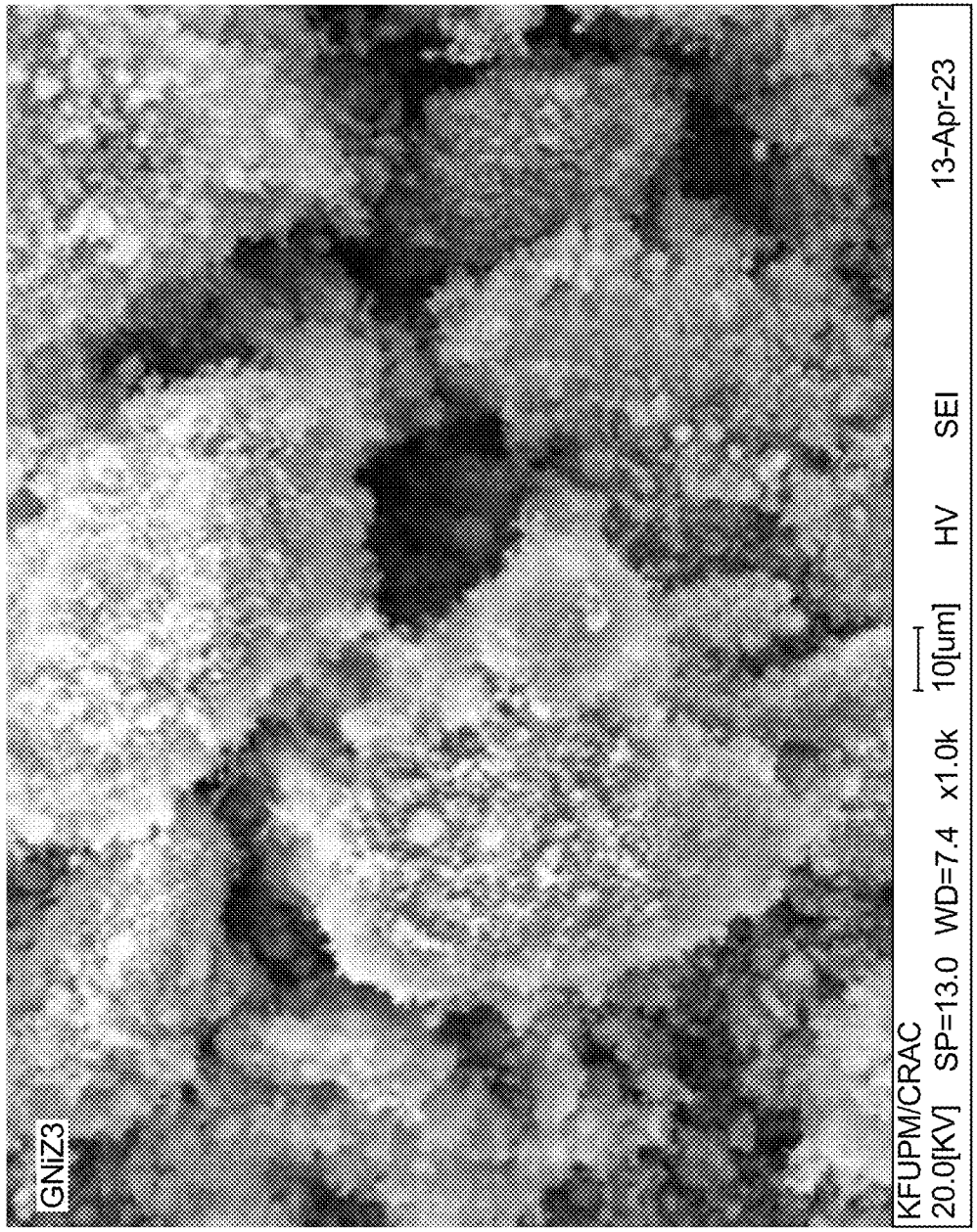
FIG. 12C is a SEM image of a GNiZ3 fresh catalyst, according to certain embodiments.
Figure 12D:
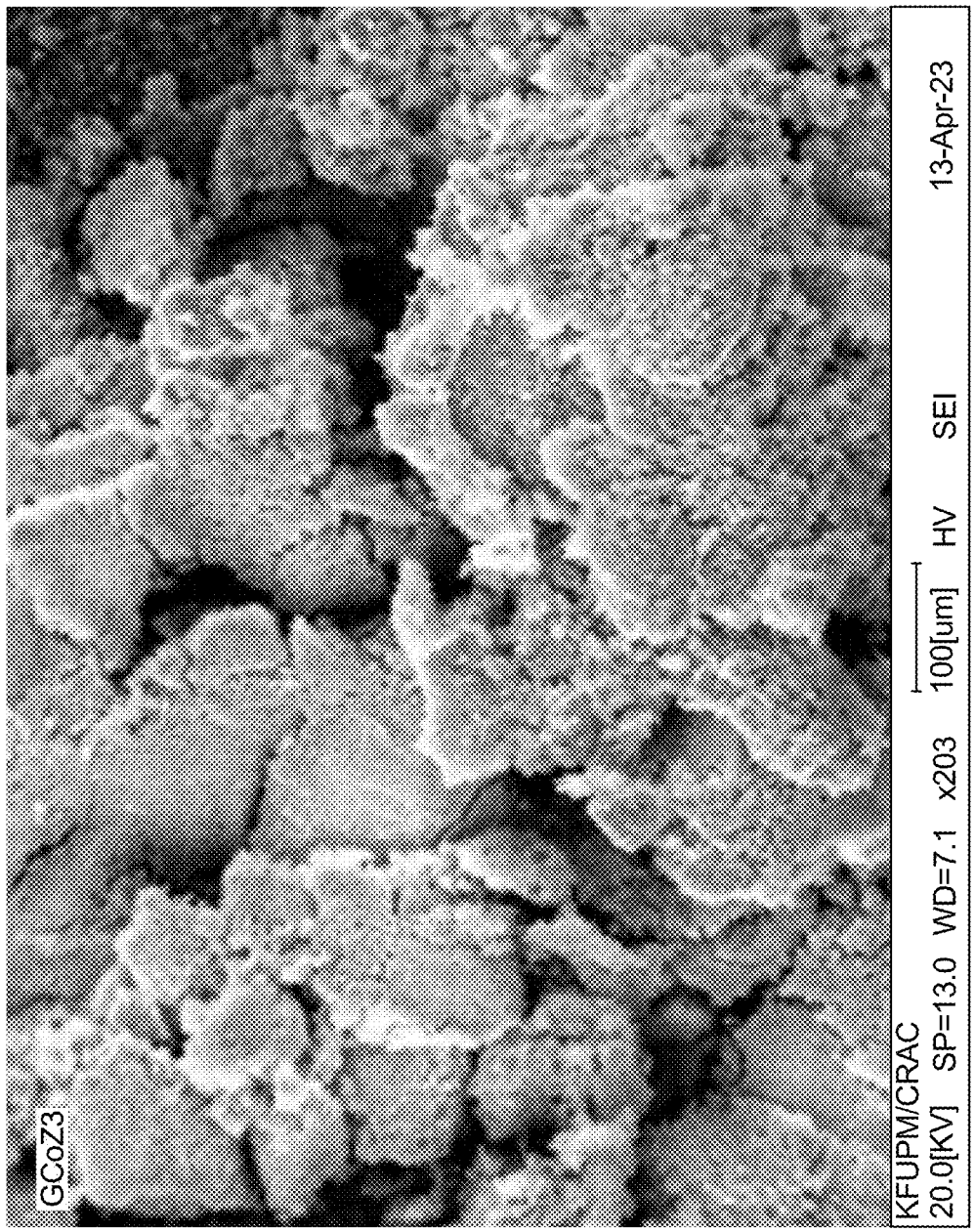
FIG. 12D is a SEM image of a GCoZ3 fresh catalyst, according to certain embodiments.
Figure 12E:
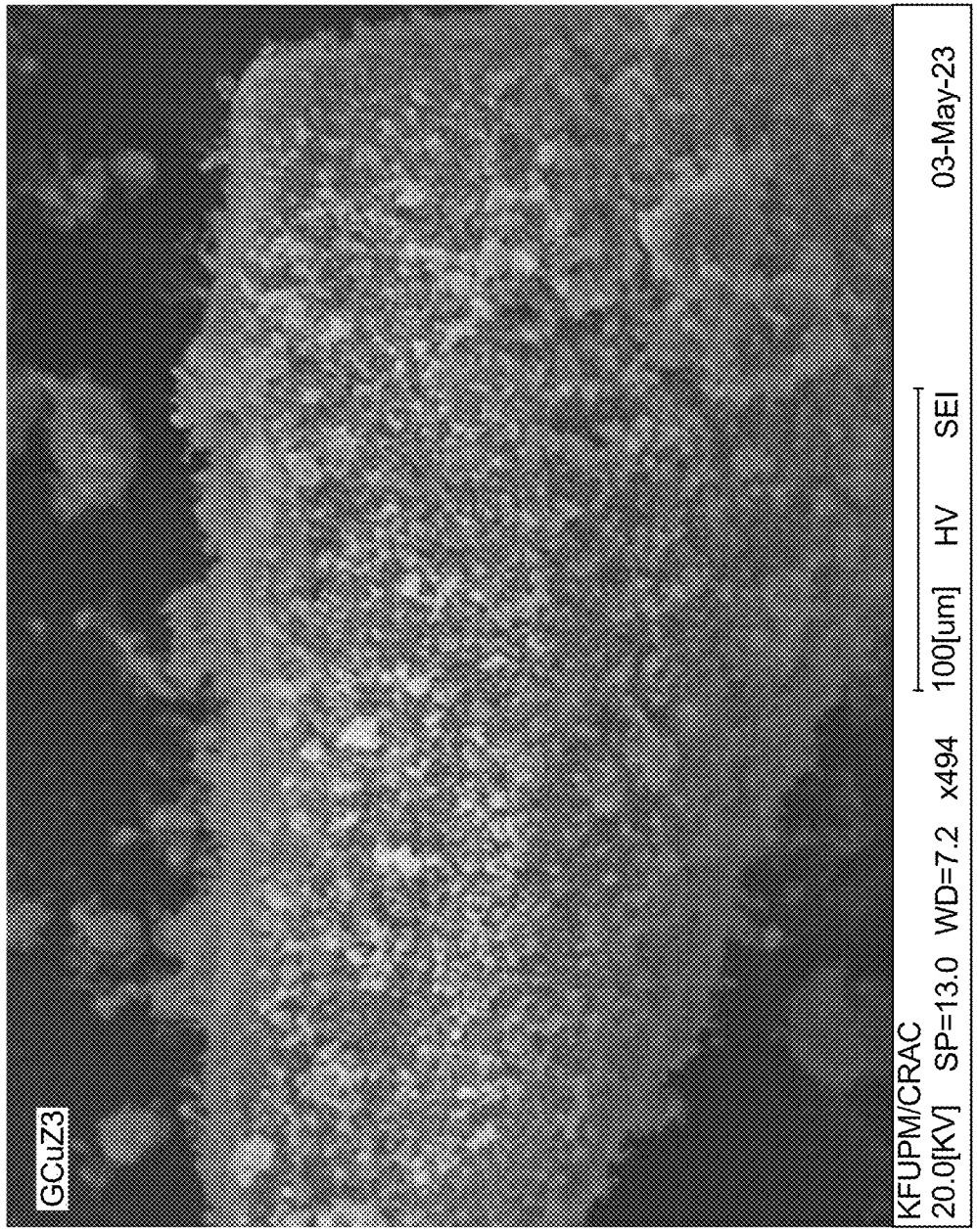
FIG. 12E is a SEM image of a GCuZ3 fresh catalyst, according to certain embodiments.

The FTIR analysis is utilized to collect the infrared spectrum of the pyrolysis oil either through transmission or absorption, enabling the identification of aliphatic and aromatic compounds. In FIG. 11, the peaks between 3100 cm$^{-1}$ to 3000 cm$^{-1}$ wavenumbers confirm the presence of '=C—H' stretch in aromatics. Further, the peaks between 1500 cm$^{-1}$ and 1400 cm$^{-1}$ are due to the presence of carbon-carbon stretching vibrations in the aromatic ring. The bands between 1250 cm$^{-1}$ and 1000 cm$^{-1}$ in frequency result from the C—H in-plane bending motion. In addition to the C—H stretching vibrations above 3000 cm$^{-1}$, two other distinct regions in the infrared spectra of aromatic compounds are used to differentiate them from non-aromatic organic compounds. Firstly, the region between 2000 cm$^{-1}$ to 1665 cm$^{-1}$ consists of weak bands known as "overtones." Secondly, the 900 cm$^{-1}$ to 675 cm$^{-1}$ region corresponds to out-of-plane vibrations.

Figure 17:
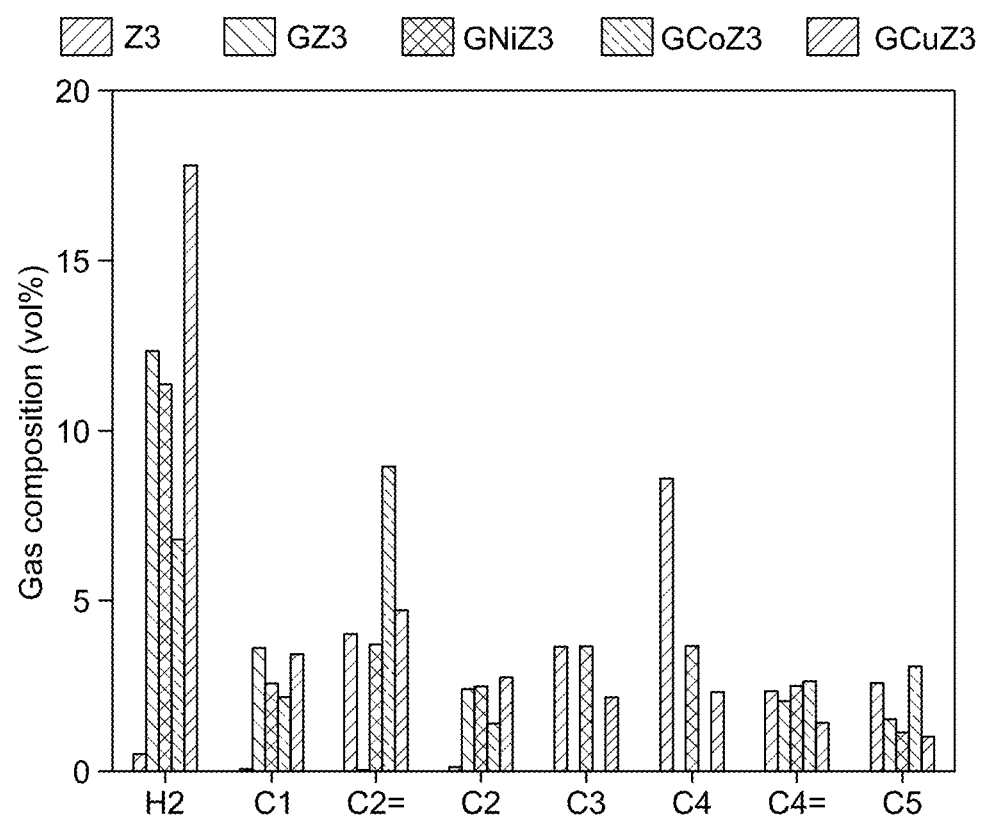
FIG. 17 is a graph depicting analysis of the evolved gases during pyrolysis, according to certain embodiments.

The composition of non-condensable gases varied by the changes of catalysts, as shown in FIG. 17. In all samples of gas products, the concentration of alkanes (C1-C5) was found to be higher than that of olefins (C2=, C4=). However, the catalytic pyrolysis of LDPE was observed to yield light olefin products predominantly through an end-chain cracking mechanism. As a result, the formation of alkanes was primarily attributed to secondary reactions, specifically hydrogen transfer reactions of olefins. Therefore, it can be said that although the initial product distribution favored the production of olefins, subsequent reactions led to an increased concentration of alkanes in the gas products. The GCuZ3 sample results in large quantities of hydrogen gas. In general, when aromatic content is high, hydrogen content in the gas product is also high, and this is understandable from the carbon-to-hydrogen ratio of aromatic and aliphatic compounds. Further, aromatic compounds hold lower hydrogen content than aliphatic compounds. Furthermore, hydrogen is always surplus and released as molecular hydrogen when the reaction proceeds through dehydrogenation and cyclization to form aromatics.

Regarding the formation of ethylene and butane and reduction of hydrogen gas while utilizing Z3, the cracking occurs significantly on the catalyst Z3, which is a zeolite acidic catalyst. Cracking produces a large amount of smaller hydrocarbon molecules, and if they subsequently crack, they end up as paraffins and lower olefins. Since there are no metals with dehydrogenation, isomerization, and cyclization functions, the reaction does not significantly or never proceed to form aromatics. This suppresses the formation of hydrogen.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of converting a polymer, comprising:
    contacting a catalyst with a low-density polyethylene polymer to form a mixture; and
    heating the mixture to a temperature of 200-600° C. in a microwave reactor to form a product,
    wherein the product comprises 20-99 weight % gas and 1-30 weight % liquid based on a total weight of the gas, the liquid and coke in the product,
    wherein the catalyst comprises an HZSM-5 zeolite, comprising:
    1-10 wt. % gallium, and
    0.1-5 wt. % copper, based on a total weight of the catalyst.

2. The method of claim 1, wherein the catalyst has a BET surface area of 250-350 m²/g.

3. The method of claim 1, wherein the catalyst has a pore volume of 0.01-0.1 cm³/g.

4. The method of claim 1, wherein the catalyst is crystalline.

5. The method of claim 1, wherein the gallium and the copper are present in pores of the HZSM-5 zeolite.

6. The method of claim 1, wherein the catalyst comprises 50-60 wt. % O, 30-40 wt. % Si, 1-5 wt. % Al, 1-10 wt. % Ga and 0.1-5 wt. % Cu, based on a total weight of the catalyst.

7. The method of claim 1, wherein particles of the catalyst have an average size of 1-100 μm.

8. The method of claim 1, wherein the catalyst is in the form of aggregated particles.

9. The method of claim 1, wherein the mixture comprises a weight ratio of the catalyst to the low-density polyethylene polymer of 1-15 to 1-15.

10. The method of claim 1, wherein the heating is conducted in an absence of oxygen.

11. The method of claim 1, wherein the heating is conducted for 1-60 minutes.

12. The method of claim 1, wherein the mixture further comprises at least one selected from the group consisting of silicon carbide, activated carbon, graphite, and alumina.

13. The method of claim 1, wherein the product comprises less than 1 weight % coke.

14. The method of claim 1, wherein the gas is at least one selected from the group consisting of hydrogen, an alkane having 1-5 carbons, and an olefin having 2-4 carbons.

15. The method of claim 1, wherein the liquid is at least one selected from the group consisting of aromatic compounds having 9-12 carbons, aromatic compounds having 13-17 carbons, olefins having greater than 9 carbons, paraffins having greater than 9 carbons, and other aliphatics.

16. The method of claim 1, wherein the liquid comprises about 90 weight % aromatic compounds having 9-12 carbons.

17. The method of claim 1, wherein the gas is 15-20 vol. % hydrogen, based on a total volume of the gas.

18. The method of claim 17, wherein the hydrogen is collected and used to power the microwave reactor.

19. The method of claim 1, wherein the low-density polyethylene polymer is a waste product.

20. The method of claim 1, wherein the low-density polyethylene polymer has a density of from 0.91-0.93 g/cm³, and
    wherein during the heating, the microwave reactor contains only the catalyst, a silicon carbide microwave adsorbent, the low-density polyethylene polymer and the product.

* * * * *